US012733866B2

(12) United States Patent
Stroyeck et al.

(10) Patent No.: US 12,733,866 B2
(45) Date of Patent: Sep. 15, 2026

(54) TRACKING, REPORTING, AND VISUALIZING PREGNANCY-RELATED ANALYTE DATA

(71) Applicant: Dexcom, Inc., San Diego, CA (US)

(72) Inventors: Charles R. Stroyeck, San Diego, CA (US); Sonya Frangopoulos, San Diego, CA (US); Douglas S. Kanter, San Diego, CA (US); Afshan Kleinhanzl, San Diego, CA (US); Shelbi Lyn Howard, San Diego, CA (US); Joann Nhu, San Diego, CA (US); Maren Bean, San Diego, CA (US); Kazanna C. Hames, San Diego, CA (US); Lindsey Franklin, San Diego, CA (US)

(73) Assignee: Dexcom, Inc., San Diego, CA (US)

( * ) Notice: Subject to any disclaimer, the term of this patent is extended or adjusted under 35 U.S.C. 154(b) by 291 days.

(21) Appl. No.: 18/511,729

(22) Filed: Nov. 16, 2023

(65) Prior Publication Data

US 2024/0156395 A1 May 16, 2024

Related U.S. Application Data

(60) Provisional application No. 63/384,058, filed on Nov. 16, 2022.

(51) Int. Cl.
*A61B 5/00* (2006.01)

(52) U.S. Cl.
CPC .......... *A61B 5/4343* (2013.01); *A61B 5/7435* (2013.01); *A61B 2560/0487* (2013.01)

(58) Field of Classification Search
CPC .... A61K 35/74; A61K 35/747; A61K 35/745; A61K 35/741; A61K 35/744;
(Continued)

(56) References Cited

U.S. PATENT DOCUMENTS

2004/0229848 A1* 11/2004 Demuth .............. C07D 263/06 514/408
2005/0096540 A1* 5/2005 Ooshima ................ G16Z 99/00 600/437

(Continued)

OTHER PUBLICATIONS

International Search Report and Written Opinion for Application No. PCT/US2023/080116, mailed Feb. 27, 2024, 13 pages.

*Primary Examiner* — Rayeez R Chowdhury
(74) *Attorney, Agent, or Firm* — Patterson + Sheridan, LLP

(57) ABSTRACT

Techniques for generating a user interface view including sensor data representative of analyte levels of a host are disclosed. In certain embodiments, a technique includes accessing sensor data including a plurality of analyte readings of the host during a plurality of time periods, wherein each analyte reading is indicative of an analyte level of the host at a respective time. The technique further includes generating a first user interface (UI) view comprising one or more UI elements based on the plurality of analyte levels of the host, and, in response to receiving a user selection of a pregnancy mode, automatically modifying a parameter of at least one UI element included in the one or more UI elements to reflect a pregnancy-specific parameter. The technique further includes generating a second UI view based on the plurality of analyte levels of the host and the pregnancy-specific parameter.

18 Claims, 20 Drawing Sheets

(58) Field of Classification Search
CPC ...... A61K 38/22; A61K 38/28; A61K 39/395; A61K 38/08; A61K 38/17; A61K 9/00; A61K 31/195; A61K 31/196; A61K 31/353; A61K 31/43; A61K 31/7048; A61K 39/00; A61K 45/06; A61K 31/00; A61K 31/155; A61K 31/198; A61K 31/42; A61K 9/20; A61K 9/48; A61K 36/28
See application file for complete search history.

(56) References Cited

U.S. PATENT DOCUMENTS

| | | | | |
|---|---|---|---|---|
| 2011/0201911 | A1* | 8/2011 | Johnson | G06F 3/0488 345/173 |
| 2015/0289822 | A1* | 10/2015 | Dugan | A61B 5/746 600/588 |
| 2016/0038077 | A1* | 2/2016 | Otto | A61B 5/4833 600/365 |
| 2017/0347971 | A1* | 12/2017 | Davis | G16H 40/67 |
| 2018/0353698 | A1* | 12/2018 | Saint | G16H 50/20 |
| 2019/0252079 | A1 | 8/2019 | Constantin et al. | |
| 2021/0361199 | A1* | 11/2021 | Kumar | G16H 40/67 |
| 2022/0265224 | A1 | 8/2022 | Hauptman et al. | |
| 2022/0328185 | A1* | 10/2022 | Segal | G16H 50/30 |

* cited by examiner 600
9:41
Connections
Sensor
3 days left
Available Connections
Share
Allow friends and family to view your sensor readings.
Apple Health
Share Dexcom data with Apple Health.
Pregnancy Assistant
Helps you manage your diabetes during pregnancy.
610
Glucose History Connection Profile 620
9:41
< Back 2 of 7 Cancel
Due Date
Add your due date to get helpful tips about managing diabetes during your pregnancy.
Due Date August 25, 2022
August 2022 > < >

| SUN | MON | TUE | WED | THU | FRI | SAT |
| --- | --- | --- | --- | --- | --- | --- |
| 1 | 2 | 3 | 4 | 5 | 6 | 7 |
| 8 | 9 | 10 | 11 | 12 | 13 | 14 |
| 15 | 16 | 17 | 18 | 19 | 20 | 21 |
| 22 | **23** | 24 | (25) | 26 | 27 | 28 |
| 29 | 30 | 31 | | | | |

Next

FIG. 6C 630
9:41
< Back 6 of 7 Cancel
-400
-300
-200
-100
-40
Target Range
The target range is your goal for your sensor reading. It's shown as a grey rectangle on the glucose graph.
Pregnancy Setting
Target Range 65-140 mg/dL
The default target range for Pregnancy Assistant is 65 -140 mg/dL.
More information
635
Confirm

FIG. 6D 640
9:41
Targe Range Done
Target Range
Target range is shown on trend graph so you can compare your readings to the internationally recommended target glucose ranges for pregnancy:

Very High: Above 250 mg/dL
Target Range: 65-140 mg/dL
Very Low: Below 54 mg/dL

Ask your healthcare provider for your recommended range.

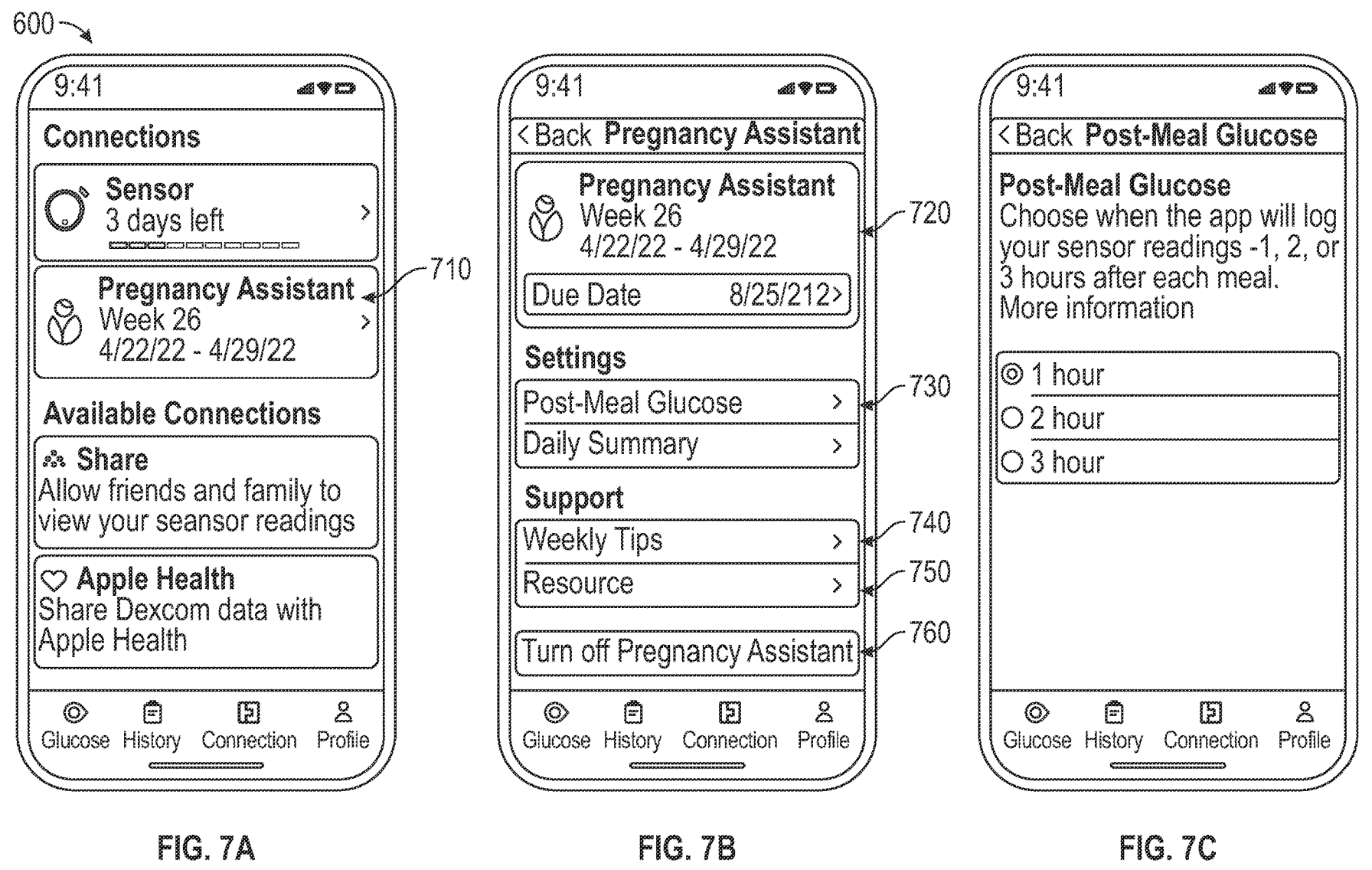

9:41
Connections
Sensor
3 days left
710
Pregnancy Assistant
Week 26
4/22/22 - 4/29/22
Available Connections
Share
Allow friends and family to view your seansor readings
Apple Health
Share Dexcom data with Apple Health
Glucose History Connection Profile

FIG. 7A 720
730
740
750
760
9:41
< Back Pregnancy Assistant
Pregnancy Assistant
Week 26
4/22/22 - 4/29/22
Due Date 8/25/212 >
Settings
Post-Meal Glucose >
Daily Summary >
Support
Weekly Tips >
Resource >
Turn off Pregnancy Assistant
Glucose History Connection Profile

FIG. 7B

9:41
< Back Post-Meal Glucose
Post-Meal Glucose
Choose when the app will log your sensor readings -1, 2, or 3 hours after each meal.
More information
1 hour
2 hour
3 hour
Glucose History Connection Profile

FIG. 7C

TRACKING, REPORTING, AND VISUALIZING PREGNANCY-RELATED ANALYTE DATA

CROSS-REFERENCE TO RELATED APPLICATION

This application claims benefit of and priority to U.S. Provisional Application No. 63/384,058, filed Nov. 16, 2022, which is assigned to the assignee hereof and hereby expressly incorporated herein in its entirety as if fully set forth below and for all applicable purposes.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a patient with diabetes carries a self-monitoring blood glucose (SMBG) monitor, which may require uncomfortable finger pricking methods. Due to the lack of comfort and convenience, a patient with diabetes will normally only measure his or her glucose level two to four times per day. Unfortunately, these time intervals are spread so far apart that the patient will likely be alerted to a hyperglycemic or hypoglycemic condition too late, sometimes incurring dangerous side effects as a result. In fact, it is unlikely that the patient will take a timely SMBG value, and further the patient will not know if his blood glucose value is going up (higher) or down (lower), due to limitations of conventional methods.

Consequently, a variety of non-invasive, transdermal (e.g., transcutaneous) and/or implantable sensors are being developed for continuously detecting and/or quantifying blood glucose values. Generally, in a diabetes management system, a transmitter associated with the sensor wirelessly transmits raw or minimally processed data for subsequent display and/or analysis at one or more display devices, which can include a mobile device, a server, or any other type of communication devices. A display device, such as a mobile device, may then utilize a trusted software application (e.g., approved and/or provided by the manufacturer of the sensor), which takes the raw or minimally processed data and provides the user with information about the user's blood glucose levels. Because diabetes management systems using such implantable sensors can provide more up-to-date information to users, they may reduce the risk of a user failing to regulate the user's blood glucose levels.

This background is provided to introduce a brief context for the summary and detailed description that follow. This background is not intended to be an aid in determining the scope of the claimed subject matter nor be viewed as limiting the claimed subject matter to implementations that solve any or all of the disadvantages or problems presented above.

SUMMARY

Certain embodiments provide a method for generating a user interface view including sensor data representative of analyte levels of a host. The method includes accessing sensor data including a plurality of analyte readings of the host during a plurality of time periods, wherein each analyte reading is indicative of an analyte level of the host at a respective time. The method further includes generating a first user interface (UI) view comprising one or more UI elements based on the plurality of analyte levels of the host, and, in response to receiving a user selection of a pregnancy mode, automatically modifying a parameter of at least one UI element included in the one or more UI elements to reflect a pregnancy-specific parameter. The method further includes generating a second UI view based on the plurality of analyte levels of the host and the pregnancy-specific parameter.

Certain embodiments provide a method for generating a user interface view including sensor data representative of analyte levels of a host. The method includes accessing sensor data including a plurality of analyte readings of the host during a plurality of time periods, wherein each analyte reading is indicative of an analyte level of the host at a respective time. The method further includes generating a first user interface (UI) view comprising one or more UI elements based on the plurality of analyte levels of the host, and, in response to receiving a user selection of a pregnancy mode, automatically modifying at least one UI element included in the one or more UI elements to reflect pregnancy-specific information. The method further includes generating a second UI view based on the plurality of analyte levels of the host and the pregnancy-specific information.

BRIEF DESCRIPTION OF THE DRAWINGS

FIGS. 6A-6E illustrate an onboarding sequence that is presented to a user when enabling a pregnancy assistant, according to certain embodiments disclosed herein.

FIGS. 7A-7H illustrate various user interface (UI) dashboards for enabling a pregnancy assistant and viewing pregnancy-specific information, according to certain embodiments disclosed herein.

DETAILED DESCRIPTION

Figure 1:
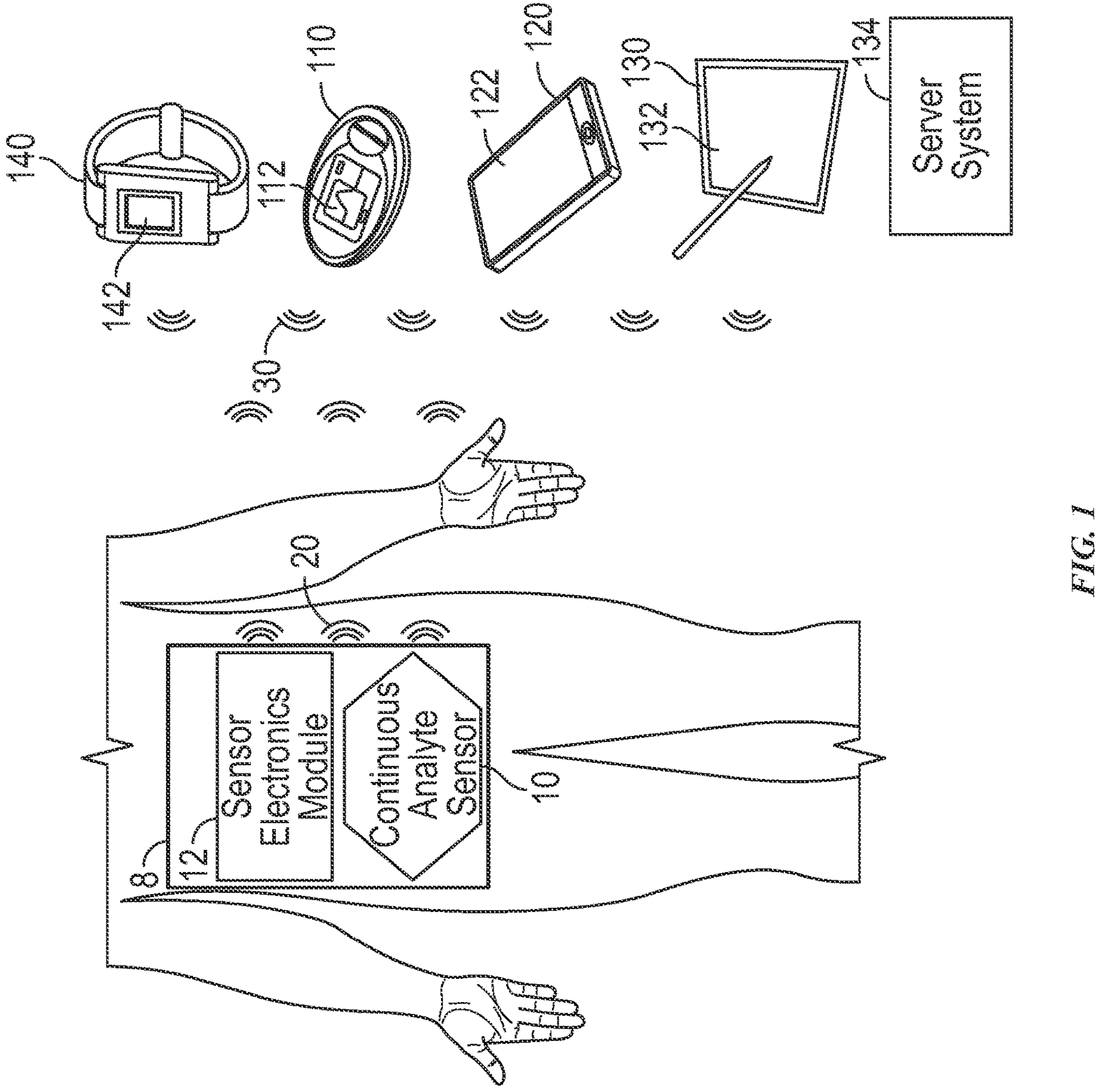
FIG. 1 depicts a health management system that may be used in connection with certain embodiments of the present disclosure.

Hormonal changes experienced during pregnancy can have a significant impact on glucose levels, insulin resistance, and/or overall diabetes management. In addition, poor glycemic control for women who have diabetes during pregnancy can lead to health complications for both the mother and the baby. Consequently, pregnant patients with diabetes are commonly asked to track various metrics (e.g., fasting glucose, postprandial glucose, etc.) and report such metrics to their healthcare provider (HCP).

Tracking of key metrics typically must be performed manually (e.g., with paper or digital logs) multiple times per day. Because such tracking is tedious and time-consuming, and due to the additional stress and burden experienced during pregnancy, pregnant patients may forget to track key metrics and/or may forget to bring their logs to appointments with their HCP. Accordingly, improved techniques for tracking and reporting pregnancy-related information are needed.

Various embodiments of the present disclosure include techniques for tracking, reporting, and visualizing pregnancy-related information, such as pregnancy-specific analyte data and educational information. Aspects include generating a user interface (UI) view (e.g., a report) based on analyte data, for example, continuous glucose monitoring (CGM) data and/or information inputted by a user. The report may include analyte concentration levels of the user for one or more timeframes (e.g., one or more days or weeks).

In various embodiments, the user is provided with an option to enable a pregnancy assistant. Selecting the pregnancy assistant causes an onboarding sequence to be displayed to the user, enabling the user to input a due date for the pregnancy. Then, upon enabling the pregnancy assistant, one or more user interface (UI) elements are automatically modified to reflect pregnancy-specific information, such as pregnancy-specific target analyte ranges. For example, enabling the pregnancy assistant may cause a target glucose concentration range displayed in one or more widgets of a UI view to be automatically modified to reflect a pregnancy-specific target glucose concentration range. Pregnancy reports (e.g., weekly reports) may then be generated based on the pregnancy-specific target glucose concentration range and shared (e.g., automatically) with the user and/or HCP. Additionally, the user may be provided with useful information (e.g., pregnancy-specific educational material) that is specific to the current gestational age.

Once the pregnancy is over, the pregnancy assistant may be disabled by the user, causing the one or more UI elements to be automatically modified to reflect a normal (non-pregnancy-specific) state. For example, a UI view implementing a pregnancy-specific target glucose concentration range may be automatically modified to reflect a normal, non-pregnancy target glucose concentration range upon disabling the pregnancy assistant. In various embodiments, the pregnancy assistant may be disabled automatically on the due date, within a predetermined period of time after the due date has passed, or upon detecting that the user has given birth (e.g., based on detecting changes to one or more analyte values of the user).

The above techniques for tracking, reporting, and visualizing pregnancy-related analyte data are described below in additional detail in conjunction with FIGS. 1-12. It should be noted that, although certain embodiments herein are described with respect to the management of diabetes, a glucose sensor system, and the transmission of glucose measurements between the devices, the protocols and techniques described herein are similarly applicable to any type of health management system that includes any type of analyte sensor(s) (e.g., lactate sensor, ketone sensor, $O_2$ sensor, etc.).

Example Analyte Sensor System

FIG. 1 depicts a health management system 100 ("system 100"), such as a diabetes management system, that may be used in connection with certain embodiments of the present disclosure. Certain embodiments involve transmission of analyte data with the health management system 100. Health management system 100 depicts aspects of analyte sensor system 8 (hereinafter "SS 8") that may be communicatively coupled to display devices 110, 120, 130, and 140, and/or to server system 134.

In certain embodiments, SS 8 is provided for measurement of an analyte in a host or a user. By way of an overview and an example, SS 8 may be implemented as an encapsulated microcontroller that makes sensor measurements, generates analyte data (e.g., by calculating values for continuous glucose monitoring data), and engages in wireless communications (e.g., via Bluetooth and/or other wireless protocols) to send such data to remote devices, such as display devices 110, 120, 130, 140 and/or server system 134. U.S. App. No. 2019/0336053, which is incorporated herein in its entirety by reference, further describes an on-skin sensor assembly that, in certain embodiments, may be used in connection with SS 8.

In certain embodiments, SS 8 includes sensor electronics circuitry 12 and an analyte sensor 10 associated with sensor electronics circuitry 12. In certain embodiments, sensor electronics circuitry 12 (also referred to herein as "analyte sensor electronics circuitry") includes electronic circuitry associated with measuring and processing analyte sensor data or information, including algorithms associated with processing and/or calibration of the analyte sensor data/information. Sensor electronics circuitry 12 may be physically/mechanically connected to analyte sensor 10 and can be integral with (e.g., non-releasably attached to) or releasably attachable to analyte sensor 10.

Sensor electronics circuitry 12 may also be operatively coupled to analyte sensor 10, such that the components may be electromechanically coupled to one another (e.g., (a) prior to insertion into a patient's body, or (b) during the insertion into the patient's body). Sensor electronics circuitry 12 may include hardware, firmware, and/or software that enable measurement and/or estimation of levels of the analyte in a host/user via analyte sensor 10 (e.g., which may be/include a glucose sensor). For example, sensor electronics circuitry 12 can include one or more potentiostats, a power source for providing power to analyte sensor 10, other components useful for signal processing and data storage, and a telemetry module for transmitting data from the sensor electronics circuitry to one or more display devices. For example, SS 8 can wirelessly transmit 20 data to a display device 110, 120, 130, 140, and a display device 110, 120, 130, 140 can wirelessly transmit 30 data to SS 8. Electronics can be affixed to a printed circuit board (PCB) within SS 8, or platform or the like, and can take a variety of forms. For example, the electronics can take the form of an integrated circuit (IC), such as an Application-Specific Integrated Circuit (ASIC), a microcontroller, a processor, and/or a state machine.

Sensor electronics circuitry 12 may include sensor electronics that are configured to process sensor information, such as sensor data, and generate transformed sensor data and displayable sensor information. Examples of systems and methods for processing sensor analyte data are described in more detail herein and in U.S. Pat. Nos. 7,310,544 and 6,931,327 and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0208245, all of which are incorporated herein by reference in their entireties.

Analyte sensor 10 is configured to measure a concentration or level of the analyte in the host. The term analyte is further defined by U.S. App. No. 2019/0336053. In some embodiments, analyte sensor 10 is a subcutaneous, transdermal (e.g., transcutaneous), or intravascular device. Analyte sensor 10 can use any method of analyte-measurement, including enzymatic, chemical, physical, electrochemical, spectrophotometric, polarimetric, calorimetric, iontophoretic, radiometric, immunochemical, and the like. Additional details relating to a continuous glucose sensor are provided in paragraphs [0072]-[0076] of U.S. application Ser. No. 13/827,577. Paragraphs [0072]-[0076] of U.S. application Ser. No. 13/827,577 are incorporated herein by reference. In certain embodiments, analyte sensor 10 is a glucose sensor. However, any other analyte sensor, such as a potassium sensor, a lactate sensor, an ammonia sensor, a creatinine sensor, or the like, are all within the scope of the disclosure. In some embodiments, analyte sensor 10 may be a multi-analyte sensor configured to sense multiple analytes (e.g., glucose, potassium, lactate, and/or others).

With reference to FIG. 1, display devices 110, 120, 130, and/or 140 can be configured for displaying (and/or alarming) displayable sensor information that may be transmitted by sensor electronics circuitry 12 (e.g., in a customized data package that is transmitted to the display devices based on their respective preferences). Each of display devices 110, 120, 130, or 140 may respectively include a display such as touchscreen display 112, 122, 132, and/or 142 for displaying sensor information and/or analyte data to a user and/or receiving inputs from the user. For example, a graphical user interface (GUI) may be presented to the user for such purposes. In certain embodiments, the display devices may include other types of user interfaces, such as a voice user interface instead of or in addition to a touchscreen display for communicating sensor information to the user of the display device and/or receiving user inputs. In certain embodiments, one, some, or all of display devices 110, 120, 130, 140 may be configured to display or otherwise communicate the sensor information as it is communicated from sensor electronics circuitry 12 (e.g., in a data package that is transmitted to respective display devices), without any additional prospective processing required for calibration and/or real-time display of the sensor data.

The plurality of display devices 110, 120, 130, 140 depicted in FIG. 1 may include a custom or proprietary display device, for example, analyte display device, especially designed for displaying certain types of displayable sensor information associated with analyte data received from sensor electronics circuitry 12 (e.g., a numerical value and/or an arrow, in certain embodiments). In certain embodiments, one of the plurality of display devices 110, 120, 130, 140 includes a smartphone, such as display device 150, based on an Android, iOS, or another operating system configured to display a graphical representation of the continuous sensor data (e.g., including current and/or historic data). In certain embodiments, health management system 100 further includes a medical delivery device (e.g., an insulin pump or pen). Sensor electronics circuitry 12 may be configured to transmit sensor information and/or analyte data to medical delivery device. The medical delivery device (not shown) may be configured to administer a certain dosage of insulin or another medicament to the user based on the sensor information and/or analyte data (e.g., which may include a recommended insulin dosage) received from the sensor electronics circuitry 12.

Figure 2:
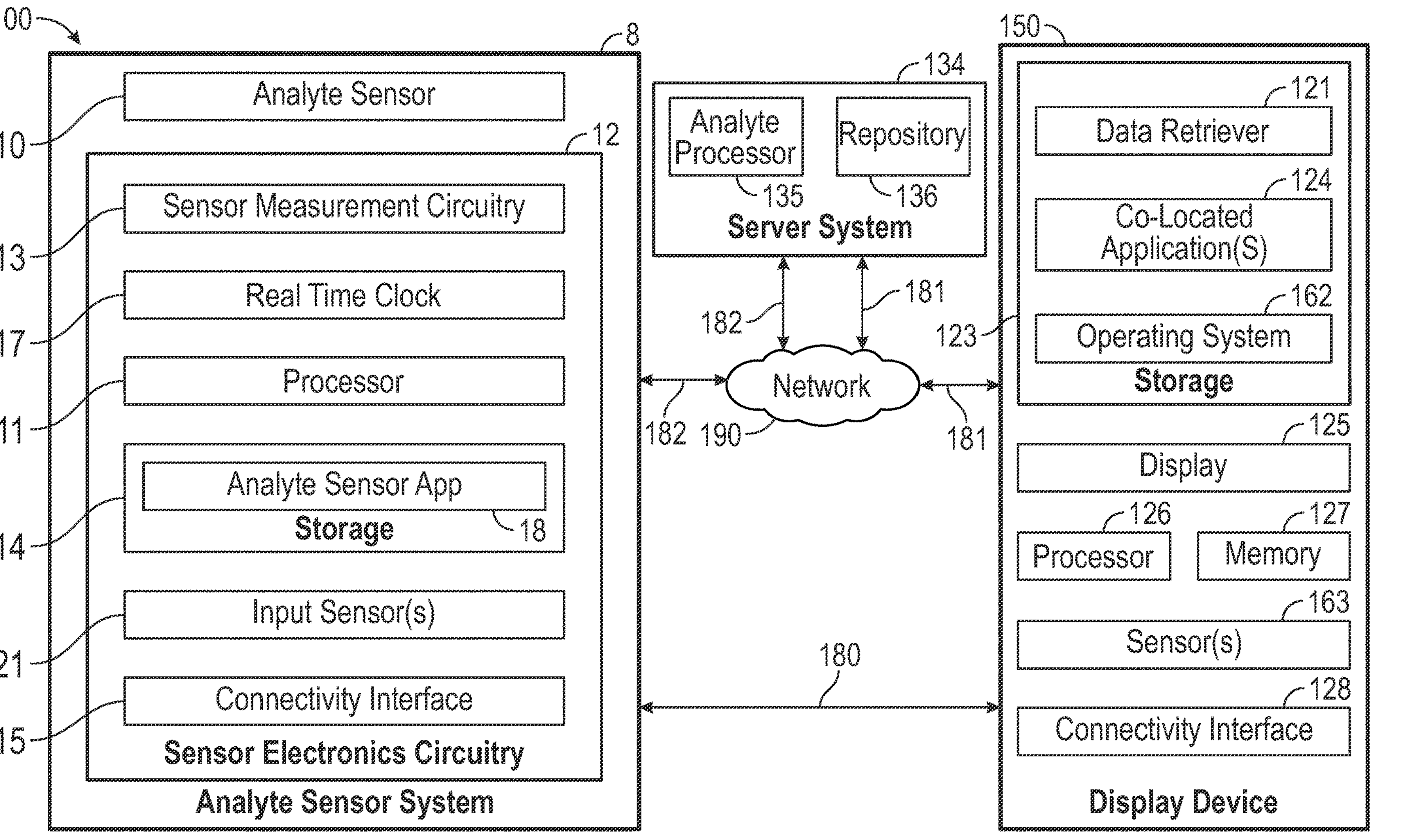
FIG. 2 illustrates the example health management system of FIG. 1 in more detail, according to certain embodiments disclosed herein.

FIG. 2 illustrates a more detailed view of health management system 100 including a display device 150 that is communicatively coupled to SS 8. In certain embodiments, display device 150 may be any one of display devices 110, 120, 130, and 140 of FIG. 1. The communication path between SS 8 and display device 150 is shown as wireless communication path 180. In certain embodiments, SS 8 and display device 150 are configured to wirelessly communicate over wireless communication path 180 using short range and/or distance wireless communication protocols.

Examples of short range and/or distance wireless communication protocols include Bluetooth and Bluetooth Low Energy (BLE) protocols. In certain embodiments, other short range wireless communications may include Near Field Communications (NFC), radio frequency identification (RFID) communications, IR (infra-red) communications, and optical communications. In certain embodiments, wireless communication protocols other than short range and/or distance wireless communication protocols may be used for wireless communication path 180, such as WiFi Direct. Display device 150 and/or SS 8 may also be configured to connect to network 190 (e.g., local area network (LAN), wide area network (WAN), the Internet, etc.). For example, display device 150 may connect to network 190 via a wired (e.g., Ethernet) or wireless (e.g., WLAN, wireless WAN, cellular, Mesh network, personal area network (PAN) etc.) interface.

Health management system 100 may additionally include server system 134, which in turn includes analyte processor 135 that is coupled to repository 136 (e.g., one or more computer storage systems, cloud-based storage systems and/or services, etc.). In certain embodiments, server system 134 may be located or execute in a public or private cloud. In certain embodiments, server system 134 is located or executes on-premises ("on-prem"). As discussed, server system 134 is configured to receive, collect, and/or monitor information, including analyte data and related information, as well as encryption/authentication information from SS 8 and/or display device 150. Such information may include input responsive to the analyte data or input (e.g., the user's glucose measurements and other physiological/behavioral information) received in connection with an analyte monitoring or sensor application running on SS 8 or display device 150. This information may be stored in repository 136 and may be processed, such as by an analytics engine capable of performing analytics on the information. An example of an analyte sensor application that may be executable on display device 150 is data retriever 121, as further described below.

Display device 150 and SS 8 are able to communicate with server system 134 through network 190. The communication path between display device 150 and server system 134 is shown as communication path 181 via network 190. The communication path between SS 8 and server system 134 is shown as communication path 182 via network 190.

In some aspects, analyte processor 135 included in server system 134 is configured to analyze analyte data (and/or other patient related data) provided via network 190. As later described in further detail in conjunction with FIG. 4, in certain embodiments, analyte processor 135 is a cloud-based processor that is configured to analyze analyte data associated with the user received through network 190 from SS 8 and/or other devices, such as display devices 110, 120, 130, and/or 140 and the like, and generate reports providing high-level information, such as statistics, regarding the measured analyte over a certain time frame. In embodiments in which the analyte processor 135 is a cloud-based processor, the generated reports may be provided, in the form of one or more user interface (UI) views, to one or more UIs (e.g., UIs 410A-C of FIG. 4) of display devices 110, 120, 130, and/or 140.

Figure 4:
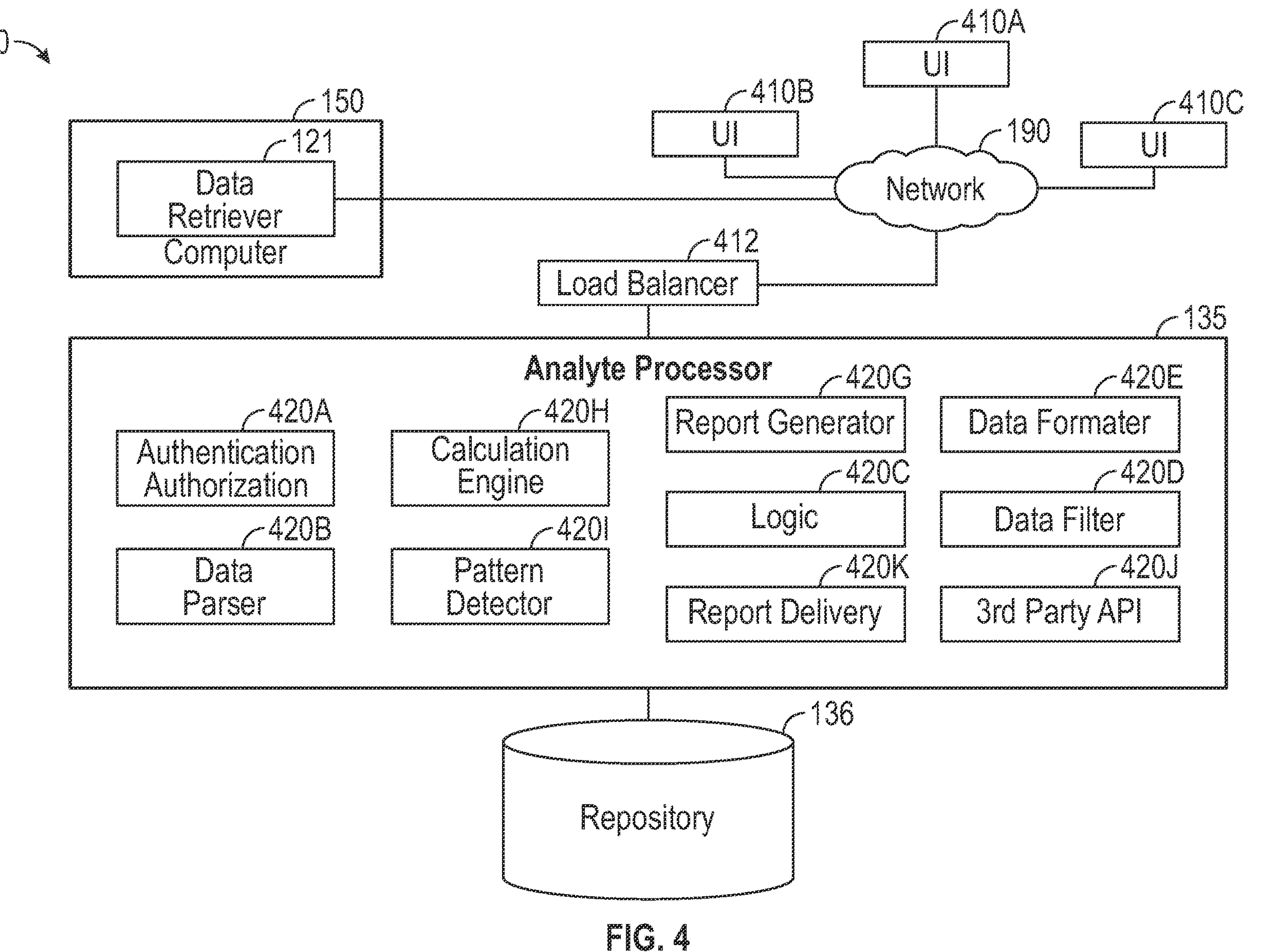
FIG. 4 is a block diagram conceptually illustrating an example analyte processing system, according to certain embodiments disclosed herein.

Although not shown in FIG. 4, in certain embodiments, the analyte processor 135 may implemented by one of display devices 110, 120, 130, or 140 that is configured to process analyte data received from SS 8 and/or other devices, such as the other display devices. In such embodiments, analyte processor 135 receives analyte data (e.g., directly) from SS 8 and generates the UI views, reports, etc., described herein. In yet other embodiments, some of functionalities 420A-420J of analyte processor 135 may be executed by one or more of display devices 110, 120, 130, and 140 while the remaining functionalities may be executed by a cloud-based server (e.g., server system 134).

In some aspects, analyte processor 135 or a report generator included therein may generate a view for display at a user interface and/or for display on one or more widgets at a user interface. The user interface view may include one or more graphical representations comprising a plurality of different graphically distinct elements representative of processed analyte data and/or other information.

In some aspects, system 100 may generate performance reports and/or user interface views dynamically. For example, the analyte processor 135 may receive a request to generate a report or a user interface view. In response to the request, the analyte processor 135 may then select the reports and/or interface views to provide. In certain embodiments, this selection may be performed based on metadata. The metadata may include information about the request, information about or representative of the user (e.g., user's personal information, user's analyte information as provided by SS 8, etc.), the type of device being used to display the report and/or measure the analyte concentration level, rules, and the like. The selection may be considered dynamic in the sense that the report and/or user interface view selection varies for each request based on metadata. The report or user interface view may then be generated to include at least one selected report and/or user interface view and then provided to a user interface for presentation.

FIG. 2 further illustrates the components of SS 8 in further detail. As shown, in certain embodiments, SS 8 includes analyte sensor 10 coupled to sensor electronics circuitry 12. Sensor electronics circuitry 12 includes sensor measurement circuitry (SMC) 13 that is coupled to analyte sensor 10 for processing and managing sensor data. SMC 13 may also be coupled to processor 11. In some embodiments, processor 11 may perform part or all of the functions of the SMC 13 for obtaining and processing sensor measurement values from analyte sensor 10. Processor 11 may also be coupled to storage 14 and real time clock (RTC) 17 for storing and tracking sensor data. Processor 11 may further be coupled to one or more input sensor(s) 21 for detecting user input.

In some embodiments, the obtaining and processing of sensor measurement values and/or user input may be managed by an analyte sensor application 18 stored in storage 14. For example, as shown, storage 14 stores analyte sensor application 18 that, when executed using processor 11, causes the processor 11 to receive and process sensor measurement values from analyte sensor 10. In some embodiments, analyte sensor application 18 is implemented as firmware that is executed by processor 11 to provide control of hardware elements (e.g., input sensor(s) 21, connectivity interface 15, RTC 17, SMC 13, etc.) included in SS 8. It is contemplated that, in some embodiments, the SMC 13 may carry out all the functions of the processor 11 and vice versa.

Transceiver 16 may be configured with the necessary hardware and wireless communications protocols for enabling wireless communications between SS 8 and other devices, such as display device 150 and/or server system 134. For example, as described above, transceiver 16 may be configured with the necessary hardware and communication protocols to establish a Bluetooth or BLE connection with display device 150. In some embodiments where SS 8 is configured to establish an independent communication path with server system 134, transceiver 16 may be configured with the necessary hardware and communication protocols (e.g., long range wireless cellular communication protocol, such as, GSM, CDMA, LTE, VoLTE, 3G, 4G, and 5G communication protocols, WiFi communication protocols, such as 802.11 communication protocols, etc.) for establishing a wireless connection to network 190 to connect with server system 134. As discussed elsewhere, other short range protocols, may also be used for communication between display device 150 and a SS 8 such as NFC, RFID, etc.

FIG. 2 similarly illustrates the components of display device 150 in further detail. As shown, display device 150 includes connectivity interface 128, processor 126, memory 127, one or more sensor(s) 163, a display 125 for presenting a graphical user interface (GUI), and a storage 123. A bus (not shown here) may be used to interconnect the various elements of display device 150 and transfer data between these elements. Connectivity interface 128 is configured to receive sensor data from SS 8 and send requests, instructions, and/or data to SS 8 as well as server system 134. Connectivity interface 128 may include multiple transceiver modules operable on different wireless standards. For example, Connectivity interface 128 may be configured with one or more communication protocols, such as wireless communication protocol(s) for establishing a wireless communication path with network 190 and/or short range wireless communication protocol(s) (e.g., Bluetooth or BLE) for establishing a wireless communication path 180 with SS 8.

Additionally, connectivity interface 128 may in some cases include additional components for controlling radio and/or wired connections, such as baseband and/or Ethernet modems, audio/video codecs, and so on. Sensor(s) 163 may include, but is not limited to, accelerometer(s), gyroscope(s), global positioning system (GPS) sensor(s), heart rate sensor (s), etc. Note that while sensor(s) 163 are shown integral to the display device 150, in certain embodiments, one or more of sensor(s) 163 be standalone sensors (e.g., separate from the display device 150).

Processor 126 may include processor sub-modules, including, by way of example, an applications processor that interfaces with and/or controls other elements of display device 150 (e.g., connectivity interface 128, data retriever 121, co-located application(s) 124, display 125, sensor(s) 163, memory 127, storage 123, etc.). Processor 126 may include and/or be coupled to circuitry, such as logic circuits, memory, a battery and power circuitry, and other circuitry drivers for periphery components and audio components. Processor 126 and any sub-processors thereof may include logic circuits for receiving, processing, and/or storing data received and/or input to display device 150. Processor 126 and any sub-processors thereof may also include logic circuits for receiving, processing, and/or storing data to be transmitted or delivered by display device 150. As described above, processor 126 may be coupled by a bus to display 125, connectivity interface 128, storage 123, etc. Hence, processor 126 may receive and process electrical signals generated by these respective elements and thus perform various functions. By way of example, processor 126 may access stored content from storage 123 and memory 127 at the direction of data retriever 121, and process the stored content to be displayed by display 125. Additionally, processor 126 may process the stored content for transmission via connectivity interface 128 to SS 8 and/or server system 134. Display device 150 may include other peripheral components not shown in detail in FIG. 2.

In certain embodiments, memory 127 may include volatile memory, such as random access memory (RAM) for storing data and/or instructions for software programs and applications, such as data retriever 121 and co-located application(s) 124. Display 125 presents a GUI associated with operating system 162 and/or data retriever 121. In various embodiments, a user may interact with data retriever 121 via a corresponding GUI presented on display 125. By way of example, display 125 may be a touchscreen display that accepts touch input. Data retriever 121 may process and/or present analyte-related data received by display device 150 and present such data via display 125. Additionally, data retriever 121 may be used to obtain, access, display, control, and/or interface with analyte data and related messaging and processes associated with SS 8 (e.g., and/or any other medical device (e.g., insulin pump or pen) that are communicatively coupled with display device 150), as is described in further detail herein.

Storage 123 may be a non-volatile storage for storing software programs, instructions, data, etc. For example, storage 123 may store data retriever 121 that, when executed using processor 126, for example, receives input (e.g., by a conventional hard/soft key or a touch screen, voice detection, or other input mechanism), and allows a user to interact with the analyte data and related content via display 125. Similarly, storage 123 may store co-located application(s) 124 that, when executed using processor 126, for example, receives input (e.g., by a conventional hard/soft key or a touch screen, voice detection, or other input mechanism), and allows a user to interact with the other non-analyte related data and related content via display 125.

In various embodiments, storage 123 may also store user input data and/or other data collected by display device 150 (e.g., input from other users gathered via data retriever 121). Storage 123 may further be used to store volumes of analyte data received from SS 8 (or any other medical data received from other medical devices (e.g., insulin pump, pen, etc.) for later retrieval and use, e.g., for determining trends and triggering alerts.

As described above, SS 8, in certain embodiments, gathers analyte data from analyte sensor 10 and transmits the same or a modified version of the collected data to display device 150. Data points regarding analyte values may be gathered and transmitted over the life of analyte sensor 10 (e.g., in the range of 1 to 30 days or more). New measurements may be transmitted often enough to adequately monitor analyte levels. As described above, in certain embodiments, rather than having the transmission and receiving circuitry of each of SS 8 and display device 150 continuously communicate, SS 8 and display device 150 may regularly and/or periodically establish a communication channel among each other.

Thus, in such embodiments, SS 8 may, for example, communicate with display device 150 at predetermined time intervals. The duration of the predetermined time interval can be selected to be long enough so that SS 8 does not consume too much power by transmitting data more frequently than needed, yet frequent enough to provide substantially real-time sensor information (e.g., measured glucose values or analyte data) to display device 150 for output (e.g., via display 125) to the user. While the predetermined time interval is every five minutes in some embodiments, it is appreciated that this time interval can be varied to be any desired length of time. In other embodiments, the transceivers may be continuously communicating. For example, in certain embodiments, the transceivers may establish a session or connection there between and continue to communicate together until the connection is lost.

Data retriever 121 may be downloaded, installed, and initially configured/setup on display device 150. For example, display device 150 may obtain data retriever 121 from server system 134, or from another source, such as an application store or the like, via a network, e.g., network 190. Following installation and setup, data retriever 121 may be configured to access, process, and/or interface with analyte data (e.g., whether stored on server system 134, locally from storage 123, from SS 8, or any other medical device). By way of example, data retriever 121 may present a menu that includes various controls or commands that may be executed in connection with the operation of SS 8, display device 150, one or more other display devices (e.g., display device 110, 130, 140, etc.), and/or one or more other partner devices, such as an insulin pump. For example, data retriever 121 may be used to interface with or control other display and/or partner devices, for example, to deliver or make available thereto analyte data, including, for example, by receiving/sending analyte data directly to the other display and/or partner device and/or by sending an instruction for SS 8 and the other display and/or partner device to be connected.

After downloading data retriever 121, as one of the initial steps, the user may be directed by data retriever 121 to wirelessly connect display device 150 to the user's SS 8, which the user may have already placed on their body. A wireless communication path 180 between display device 150 and SS 8 allows SS 8 to transmit analyte measurements to display device 150 and for the two devices to engage in any of the other interactions described herein.

Figure 3:
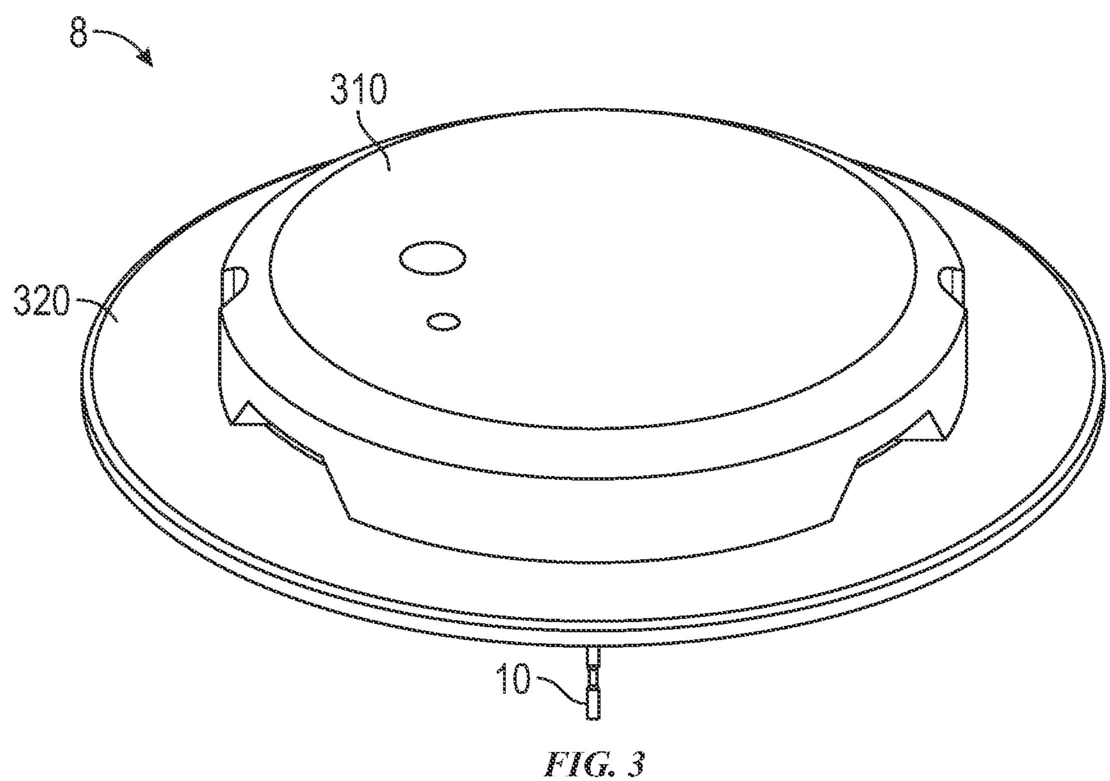
FIG. 3 illustrates a perspective view of an outer housing of the analyte sensor system of FIG. 1, according to certain embodiments disclosed herein.

FIG. 3 illustrates a perspective view of an outer housing 310 of SS 8, according to certain embodiments disclosed herein. In some embodiments, the outer housing 310 may include a clamshell design. SS 8 may further include, for example, a power source (e.g., a battery) for providing power to analyte sensor 10 and analyte sensor electronics circuitry 12.

The outer housing 310 may include aperture disposed through a portion of outer housing 210 and adapted for analyte sensor 10 and needle insertion through a bottom of SS 8. In some embodiments, the aperture may include a channel or an elongated slot. SS 8 may further include an adhesive patch 220 configured to secure SS 8 to skin of the host. The adhesive patch 220 may include an adhesive suitable for skin adhesion, for example, a pressure sensitive adhesive (e.g., acrylic, rubber-based, or other suitable type) bonded to a carrier substrate (e.g., spun lace polyester, polyurethane film, or other suitable type) for skin attachment, although any suitable type of adhesive may be implemented.

FIG. 4 is a block diagram conceptually illustrating an example analyte processing system, in accordance with some example aspects of the present disclosure. As shown in FIG. 4, the processing system 400 may include one or more user interfaces 410A-C, such as a browser, an application, a widget, and/or any other type of user interface configured to allow accessing and/or interacting with analyte processor 135 via, for example, network 190 and a load balancer 412. The analyte processor 135 may further be coupled to repository 136. User interfaces 410A-C may be associated with or provided as part of display devices 110, 120, 130, 140 and/or any other display devices used by a user to view the user interface views, reports, etc., described herein.

Processing system 400 may also receive data from source systems, such as health care management systems, patient management systems, prescription management systems, electronic medical record systems, personal health record systems, and the like. This source system information may provide metadata for dynamic report generation.

Processing system 400 may be implemented in a variety of configurations including stand-alone, distributed, and/or cloud-based frameworks. Processing system 400 may be implemented in a cloud-based framework, such as a software-as-a-service (SaaS) arrangement in which the analyte processor 135 is hosted on computing hardware, such as servers and data repositories maintained remotely from an entity's location (e.g., remote from a user, a health service provider, and like end-user) and accessed over network 190 by authorized users via a user interface, such as user interface 410A, 410B, and/or 410C, and/or a data retriever 121.

Referring again to FIG. 4, in some example aspects, processing system 400 may provide a cloud-based diabetes data management framework configured to receive patient-related data from various devices. Various devices may include, and are not limited to, a medical device, a glucose meter, a continuous glucose monitor, a SS 8, display devices 110, 120, 130, and/or 140, source systems, a device providing food consumption information (e.g., such as carbohydrates) associated with food consumed by a user, medicament delivery data, time of day, temperature sensors, and/or exercise/activity sensors. In some example aspects, the cloud-based diabetes data management may receive the data programmatically with little (or no) intervention on the part of a user.

The data received from devices, source systems, and the like, may be in a variety of formats and may be structured or unstructured. For example, in some example aspects, the processing system 400 may receive raw sensor data, which has been minimally processed or analyzed. The received data may then be formatted, processed (e.g., analyzed), and/or stored in order to enable analyte data visualization. For example, a data retriever 121 may be implemented at one or more devices, such as display device 150 coupled to SS 8. In this example, data retriever 121 may format sensor data into one or more common formats compatible with analyte processor 135 and may provide the formatted data to analyte processor 135 such that analyte processor 135 may analyze the formatted data.

Although FIG. 4 depicts a single data retriever 121, in some example aspects, a plurality of data retrievers 121 may be used to format data from a plurality of devices and/or systems. In certain embodiments, data retriever 121 may execute on or be hosted at any other one of display devices, such as display devices 110, 120, 130, and/or 140, in communication with SS 8.

The processing at analyte processor 135 may also include associating metadata with the data received from the devices and/or sensors. Examples of metadata may include, but are not limited to, patient information, keys used to encrypt the data, patient accelerometer data, location data (e.g., location of patient or location of patient's clinic), time of day, date, type of device used to generate associated sensor data. The patient information may include the patient's age, weight, sex, pregnancy due date, gestational age, home address and/or any past health-related information, such as whether the patient has been diagnosed as having type 1 or type 2 diabetes, high-blood pressure, or as having any other health condition.

In the example of FIG. 4, user interfaces 410A-C may be used by one or more entities, such as end-users, health care providers, clinics, patients, research groups, health systems, medical device manufacturers and the like. These entities may remotely access processing system 400 via user interface 410A-C (e.g., of display devices 110, 120, 130, and/or 140) to request an action, such as retrieve analyte data, provide analyte data, request analysis of analyte data, request generation of reports including modules having views presenting descriptive measurements of the analyte data, present analyte data and reports, and the like. Other examples of actions include providing sensor data, such as glucose data, carbohydrate data, insulin pump data, and the like, to the analyte processor 135, initiating processing of the sensor data, initiating analysis of the sensor data, and storing data at repository 136. In some example aspects, the computing resources provided by analyte processor 135 may comprise one or more physical servers virtualized to provide the analyte processing services disclosed herein.

In some example aspects, the analyte processor 135 may process the received data by performing one or more of the following: associate metadata with the data received from the devices, sensors, source system, and/or data retriever, determine one or more descriptive measurements, such as statistics (e.g., median, inner and outer quartile ranges, mean, sum, n, and standard deviation), validating and verifying the integrity of the received data from the devices, sensors, source system, and/or data retriever, process received data based on metadata (e.g., to select certain patients, devices, conditions, diabetic type, and the like), and/or correlate received data from the devices, sensors, source system, and/or data retriever so that the data may be compared and combined for processing and analyzing.

Moreover, the results of any processing performed by analyte processor 135 may be used to generate views presenting descriptive measurements and/or comparisons of the analyte data (e.g., user interface views depicted in FIGS. 5-11). The descriptive measurements and/or comparisons may be presented, for example, as graphs, bar graphs, static charts, charts, badges, tables, figures, maps, plots, and/or other visualizations.

Furthermore, the outputs generated by processing system 400 may be provided via one or more delivery mechanisms, such as report delivery module 420K. For example, the report delivery module 420K may provide outputs generated by analyte data processing system 400 via email, secure email, print, text, presentations for display at a user interface (such as at user interface 410A-C hosted at a tablet, phone, or other processor), machine-to-machine communications (e.g., via third party interface 420J), and any other communication mechanism.

In some example aspects, the views may be customized dynamically for use by, for example, an entity, such as an end-user, a clinician, a healthcare provider, or a device manufacturer. Furthermore, the views may be customized based on the types and/or quantity of sensors and systems providing data to processing system 400 and metadata or the types thereof available to processing system 400. This customization may be performed by a user, by processing system 400 programmatically, or a combination of both.

Analyte processor 135 may include, in some example aspects, an authenticator/authorizer 420A for authorizing access to analyte processor 135, a data parser 420B for parsing requests sent to analyte processor 135, a calculation engine 420H for receiving data from sensors and processing the received data into counts for use with histograms, logic 420C, a data filter 420D, a data formatter 420E, a report generator 420G, a pattern detector 4201, a report delivery module 420K for delivering views in a format for the destination, and a third party access application programming interface to allow other systems and device to access and/or interact with analyte processor 135.

Analyte processor 135 may receive a request from a user interface, such as user interface 410A-C, to perform an action (e.g., provide data, store data, analyze/process data, request a report, and the like). Before analyte processor 135 services the request, the analyte processor 135 may process the request to determine whether the request is authorized and authenticated. For example, authenticator and authorizer 420A may determine whether the sender of the request is authorized by requiring a user to provide a security credential (e.g., a user identifier, a password, a stored security token, and/or a verification identifier provided by text message, phone, or email) at a user interface presented on a computer. If authorized, authenticator and authorizer 420A may authenticate the sender of the request to check whether a security credential associated with sender of the request indicates that the sender (e.g., a user at user interface 410A) is indeed permitted to access a specific resource at analyte data processing system 400 in order to perform the action, such as store (or upload) data at repository 136, perform analyze/process data, and/or request user interface view generation.

Once authorized and/or authenticated, the request received at analyte processor 135 may then be parsed by data parser 420B to separate any data, such as sensor data, metadata, and the like, from the request. In some aspects, data parser 420B may perform check data formatting, device-related error codes, validity of the data, duplicate data points, and/or other aspects of the data. Moreover, the data parser 420B may associate additional metadata with the separated data. The metadata may include any of the metadata described herein, including an owner of the data, a key to track the data, an encryption key unique to each user, time of day, date information, one or more locations where the data is (or will be stored), and the like. In some example aspects, the data parsing 420 may provide data to the calculation engine 420H for formatting the data into counts and histograms as described further below.

In some example aspects, the request (or the parsed data therein) may be processed by calculation engine 420H. The calculation engine 420H may preprocess the data received from devices, sensors, and the like to form "counts." The counts may represent a measured value, such as an analyte value measured by a sensor, a glucose value measured by a sensor, a continuous glucose value measured by a sensor, and/or other diabetes related information, such as carbohydrates consumed, temperature, physical activity level, and the like, and how often that measured value occurred.

The calculation engine 420H may then use the count 508 to perform additional processing. The additional processing may include storing the count in repository 136, which may include one or more databases to store the counts. Moreover, the count may be stored with metadata, such as time of day/date information. Furthermore, the count may be encrypted, as noted, before storage in repository 136.

The calculation engine 420H may also use the count to update one or more histograms. For example, rather than keep track of and process a user's analyte levels over a certain period of time using raw sensor data values, the calculation engine 420H may convert the data values into counts. The counts may be added to histograms, for a given user. In some example aspects, the calculation engine 420H may generate a plurality of histograms for a given user for a plurality of given time periods. In some example aspects, the calculation engine 420H may also update other histograms representative of aggregate count information.

Although the description with respect to the calculation engine 420H refers to a histogram, the histogram, as used herein, refers to a data structure that includes one or more values associated with one or more time intervals. For example, the histogram may represent one or more values, such as frequency of occurrence, associated with bins corresponding to one or more time intervals. Moreover, this data structure may be stored at a database, such that the data structure is readily accessed with a read, such as in a row of a database (or, for example, in a column if a column database is used).

In some example aspects, repository 136 stores the histograms including counts in a database. For example, repository 136 may store data for a user that covers a time frame, such as 1 day, 2 days, 7 days, 14 days, 30 days, and/or any other time frame. In this example, the days may be subdivided into epochs, each of which has a corresponding histogram stored in repository 136. Moreover, each histogram may be stored as a row (or column) in a database at repository 136 to facilitate fast data access.

Logic 420C of FIG. 4 may also process requests to perform an action (e.g., store, retrieve, process, analyze, report data, etc.) at analyte processor 135. Logic 420C may also determine one or more descriptive measurements, such as statistics (e.g., a median, inner and outer quartile ranges, a mean, a sum, a standard deviation, and the like) based on counts, histograms, and/or received sensor data. The logic 420C may provide these descriptive measurements to the report generator 420G to enable report generation (e.g., generation of a view for presentation at user interfaces 410A-C). For example, the mean may be determined by summing the product of the count and the bin value and then dividing that sum by the sum of the counts.

Pattern detector 4201 of FIG. 4 may perform pattern detection on data (e.g., sensor data representative of blood glucose data, analytes, insulin pump data, carbohydrate consumption data, and the like) processed by analyte processor 135 and stored at repository 136. Moreover, the pattern detector 4201 may detect patterns retrospectively for a predetermined time period defined by processing system 400 and/or a user.

In some example aspects, the pattern detector 4201 may receive input data from the repository 136. The input data may include, for example, analyte concentration data, for example from a continuous analyte sensor, other analyte data, such as rate of change, predictive concentrations etc. In some example aspects, input data may also include other data such as temperature data, accelerometer data, insulin pump data, carbohydrate consumption data, food intake data, nutrition intake or breakdown information, time of day, exercise and/or activity data, awake/sleep time intervals, medications information, or other similar data relating to activities of the user that may impact one or more biological parameters of the user.

Moreover, the input data may comprise historical data obtained over a time frame, such as 8 hours, 1 day, 2 days, 7 days, 14 days, 30 days, and/or any other time frame. For example, the input data may include "counts" representative of monitored analyte detection levels (e.g., glucose concentration levels) received and stored at processing system 400 over a period covering a four-week (or more) time frame. As mentioned above, "counts" may be stored in repository 136 with metadata, such as time of day/date information, to be used as input data at a later time. In another example, the input data may include histograms updated by "counts" of the user. The histogram may include an x-axis of analyte concentration values and a y-axis of the number of occurrences for each analyte concentration value. The histogram associated with a given user/patient may be an example of input data used by pattern detector 4201.

The pattern detector 4201 may analyze the input data for patterns. For example, patterns may be recognized based on one or more predefined rules (also referred to as criteria or triggers). Furthermore, the one or more predefined rules may be variable and adjustable based on user input. For example, some types of patterns and rules defining patterns may be selected, turned on and off, and/or modified by a user, a user's physician, or a user's guardian, although processing system 400 may select, adjust, and/or otherwise modify rules programmatically as well. In another example aspect, one or more patterns may be based on predefined rules set by factory settings or device settings.

The pattern detector 4201 may detect the pattern and generate an output, which may be provided to report generator 420G. Moreover, the output may include a retrospective analysis of the input data and any patterns determined by pattern detector 4201.

The data filter 420D may be used to check whether an output generated by analyte processor 135, such as a response for certain types of data, a report, and the like, does not violate a data rule. For example, the data filter 420D may include a data rule to check whether a response includes data, such as PII, to a destination which is not authorized or allowed to receive the response (e.g., based upon authorization and authentication and the corresponding role of the user making the request).

The data formatter 420E may format data for delivery based on the type of destination. For example, the data formatter 420E may format a view based on whether it is being sent to a printer, a user interface, a secure email, another processor, and/or any other similar device or platform.

The report generator 420G may generate one or more reports and/or user interface views. The reports/views may provide descriptive information, such as statistical information, representative of the sensor data received at analyte processor 135. Moreover, the report/view may provide a retrospective analysis of the sensor data stored at repository 136. For example, the report/view may provide statistical information based on sensor data (and/or corresponding histograms including counts) over a time frame, such as 8 hours, 1 day, 2 days, 7 days, 14 days, 30 days, and/or any other time frame. Moreover, the report/view may allow a user to view the information and identify trends and other health related issues.

In some example aspects, report generator 420G generates reports and/or views based on data received and/or stored at processing system 400 (e.g., using sensor data, metadata, counts, histograms, information associated with a request to generate a report, and the like). For example, report generator 420G may select one or more features or modules for providing as part of UIs displayed (e.g., FIGS. 5-11) to a user based on a request received by a user to generate a report. In certain embodiments, the request may include information such as the identity of the patient, identity of the requesting device, a type of report being requested, and/or the like. The request may also specify a time frame for the report and/or as any other information required to authenticate the device requesting device or user.

The report generator 420G may also select one or more features or modules for providing as part of UIs displayed (e.g., FIGS. 5-11) to a user based on metadata including rules, templates, and/or the like. This metadata may describe one or more of the following: types of data available; amount of data; types of devices being used; user preferences; size of the user interface available to present report; patient demographics; patient information including report preferences, types and quantity of devices used, and display size being used to present the report, and other data related to the user, devices, and the like; rules, such as whether a module can be used with certain devices (for example, certain reports may only be suitable for continuous blood glucose, rather than discrete measurements), whether a module can be used with certain patient conditions (for example, a caregiver may establish a rule requiring a certain report based on whether a patient is pregnant), whether a module may be used on certain display sizes, whether a module may be used given a certain volume of data or device type; and/or one or more templates. For example, the selection of modules may be performed based on metadata including user preferences for certain modules, a type of device being used, a display area of the device, and a rule defining which modules can be used given the type of device, a patient state/condition, and the display area of the device. Furthermore, the metadata may be stored at a repository, such as repository 136, although some of the metadata or may be provided as part of the request received at 710.

A template may define the placement of one or more modules in a report. The framework defining the placement of each module may be a template (also referred to as a model or a wireframe). Moreover, templates may be defined for certain devices or displays, so that when the request is made and/or metadata obtained, the report generator 420G can dynamically select, based on metadata, one or more modules into the predefined template. For example, a certain display device may be of a size which allows four modules to be displayed in one way, while another display device may be of a size which allows the four modules to be displayed in a different way, and so forth.

In some exemplary implementations, the metadata may include a plurality of predefined templates configured for a specific patient, a specific type of patient (e.g., a pregnant patient), a specific caregiver, a specific medical professional, a group of patients (e.g., cohorts), a businessperson, and/or the like. As such, modules may be dynamically selected based on an evaluation of the metadata. Moreover, the use of the templates may, in some implementations, allow the dynamic generation of modules to be performed more rapidly, when compared to not using the templates. In any case, when the report generator 420G selects which modules 710A-D are to be included in the report, the report generator 420G may then obtain the underlying data (for example, sensor data, demographics, and the like) to be used in the selected modules. Examples of reports and/or user interface views that include features (also referred to as modules) are depicted in FIGS. 5-11.

According to certain aspects, logic 420C and pattern detector 4201 may be used to determine one or more descriptive measurements, patterns, or relationships for effective visualization. As described previously, logic 420C may determine a median, inner, and outer quartile ranges, a mean, a sum, a standard deviation, and other statistical measurements based on counts, histograms, and/or received sensor data. Pattern detector 4201 may analyze relationships among the data to determine patterns. Relationships in the input data that may result in an identified pattern may include, for example, an analyte level that exceeds a target analyte range (e.g., which may be defined by a user, a health care provider, processing system 400, based on whether a patient is pregnant, or a combination thereof), an analyte level that is below a target analyte range, a rapid change in analyte levels from low to high (or vice versa), times of day when a low, a high, an at range, or rapid analyte level event occurs, days when a low, a high, an at range, and/or a rapid analyte level event occurs.

Additional examples of the types of relationships in the input data that may be considered a pattern include very high and/or very low analyte events by time of day. As an example, in aspects where the analyte for measurement may be glucose, a pattern may be identified in situations where the user has low analyte concentrations around the same time in the day (e.g., a hypoglycemic event). Another type of pattern, which may be identified, is a "rebound high" situation. For example, a rebound high may be defined as a situation where a user overcorrects a hypoglycemic event by overly increasing glucose intake, thereby going into a hyperglycemic event. These events may be detected based on one or more predefined rules. Patterns that may be detected include a hyperglycemic pattern, a hypoglycemic pattern, patterns associated with a time of day or week, a weighted scoring for different patterns based on frequency, a sequence, and a severity.

In some aspects, patterns may be based on whether a patient is pregnant, a gestational age of the pregnancy, a due date of the pregnancy, a custom sensitivity of a user/patient, a transition from a very low to a very high pattern, an amount of time spent in a severe event, and a combination of analyte change and time information. Detected patterns may also be patterns of high variability of analyte data. Further, a pattern may be based on a combination of previous pattern data and a currently detected situation, whereby the combined information generates a predictive alert.

Figure 5:
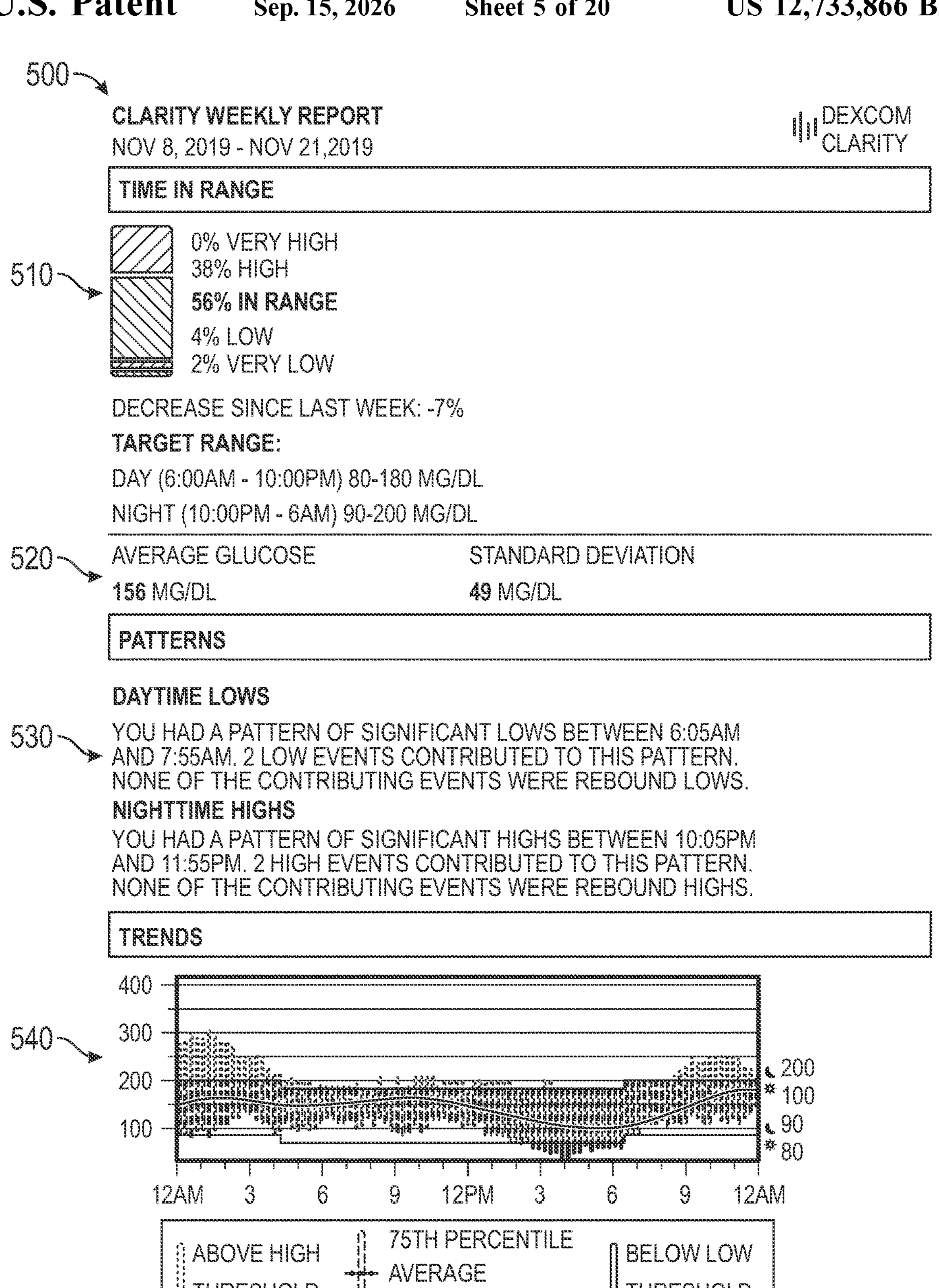
FIG. 5 illustrates an example user interface view associated with sensor data representative of analyte levels, according to certain embodiments disclosed herein.

FIG. 5 illustrates an example user interface view 500 associated with sensor data representative of analyte level(s), specifically glucose concentration level(s), in a user, in accordance with some example aspects of the present disclosure. Patterns and statistics identified by logic 420C and pattern detector 4201 may be presented in a performance report. As shown in FIG. 5, a weekly report may be provided to a user of a diabetes management application to provide relevant insights into a user's retrospective glucose values, patterns, and trends over time.

In a time in range feature 510 of the user interface view 500, a time in range stacked bar graph, representing a percentage of time the user was in a target glucose range, a very high or high glucose range, and a very low or low glucose range over a specified period (e.g., any continuous seven day period), may be provided. The target glucose range may be defined as a different range for daytime (e.g., 6:00 AM-10:00 PM in the example shown) and nighttime (e.g., 10:00 PM-6:00 AM in the example shown) hours. The user's percentage of time in range may also be compared to the previous week's percentage of time in range.

In some examples, the stacked bar graph may be presented using different colors to differentiate the percentages of time the user was in a target glucose range, a very high or high glucose range, and a very low or low glucose range over a specified period. In some examples, the stacked bar graph may be presented using different size blocks (stacked in the stacked bar graph) for each of the ranges. The varying sizes may correlate to the amount of time the user spent in each range. For example, the largest block size in the stacked bar graph may represent the glucose range the user spent the most amount of time in over a specified period of time, while the smallest block size in the stacked bar graph may represent the glucose range the user spent the least amount of time in over a specified period of time.

In an analyte statistics feature 520 of the user interface view 500, average glucose and standard deviations statistics (e.g., determined by logic 420C) may be presented to a user. The average glucose and standard deviation may be calculated based on a specified period (e.g., any continuous seven day period).

In a user patterns feature 530 of the user interface view 500, a user's patterns of daytime lows/highs and nighttime lows/highs may be reported. A daytime or nighttime low pattern may be identified in situations where the user has a pattern of low glucose concentration levels around similar times each day in a specified period (e.g., any continuous seven day period). A daytime or nighttime high pattern may be identified in situations where the user has a pattern of high glucose concentration levels around similar times each day in a specified period (e.g., any continuous seven day period).

In a trends feature 540 of the user interface view 500, a compilation of a user's time in range may be presented in a scatter plot with a line of best fit. The line of best fit expresses the relationship between the data points and identifies a user's time in range trend over a period of time (e.g., a twelve hour period, 12:00 AM-12:00 AM in the example shown) for a specified period (e.g., any continuous seven day period). Additionally, target glucose ranges, for both daytime and nighttime hours, may be provided in the graph. The target glucose ranges may be defined as a different range for daytime and nighttime hours. For example, as shown in the fourth feature, the graph may identify a daytime target glucose range using a figure in the shape of a sun (e.g., daytime range shown in the feature is 80-180 mg/dL) and may identify a nighttime target glucose range using a figure in the shape of a moon (e.g., nighttime range shown in the feature is 90-200 mg/dL). The trends feature 540 may also provide different color bar graphs to make the distinction between a user's time in a high or very high glucose range, a user's time in a low or very low glucose range, and a user's time in glucose range over a twelve hour period for a specified period.

In some examples, the features of the user interface view 500 may be presented in a vertical format (e.g., as shown in FIG. 5) to the user such that feature one may be at the top of the page (e.g., email) and feature five may be at the bottom of the page. In other examples, any of the features of the user interface view 500 may instead be presented in a horizontal format (e.g., as shown in FIGS. 9A-9D, 10A, and 10B).

Tracking, Reporting, and Visualizing Pregnancy-Related Analyte Data

As discussed above, various embodiments described herein include techniques for tracking, reporting, and visualizing pregnancy-related information, such as pregnancy-specific analyte data and educational information. In certain embodiments, the user is provided with an option to enable a pregnancy assistant (e.g., FIG. 6A). Selecting the pregnancy assistant causes an onboarding sequence to be displayed to the user, enabling the user to input a due date for the pregnancy (e.g., FIG. 6C), to view and/or modify a target analyte range and/or one or more analyte thresholds (e.g., FIGS. 6D and 6E), and/or to set one or more alarms/alerts that remind the user to log fasting glucose concentration values and/or postprandial glucose concentration values.

Upon enabling the pregnancy assistant, one or more user interface (UI) elements are automatically modified to reflect pregnancy-specific information, such as pregnancy-specific target analyte ranges and/or analytes threshold(s), pregnancy-specific widgets, and/or pregnancy-specific educational information (e.g., FIGS. 7B and 7E-7G). For example, one or more features included in user interface view 500 (e.g., time in range feature 510 and trends feature 540) may be modified to reflect pregnancy-specific information, such as a pregnancy-specific target glucose range (e.g., FIGS. 9A-9C). Enabling the pregnancy assistant may further cause assistance to be provided to the user in recording key metrics related to managing diabetes during pregnancy, such as by display reminders to log fasting glucose concentration values and post-meal glucose concentration values (also referred to as postprandial glucose concentration values) and/or by calculating fasting glucose concentration values based on wake-up times that have been selected by the user. In certain embodiments, information (e.g., pregnancy-specific educational material) provided by the UI is updated over the course of the pregnancy based on gestational age.

Figure 10A:
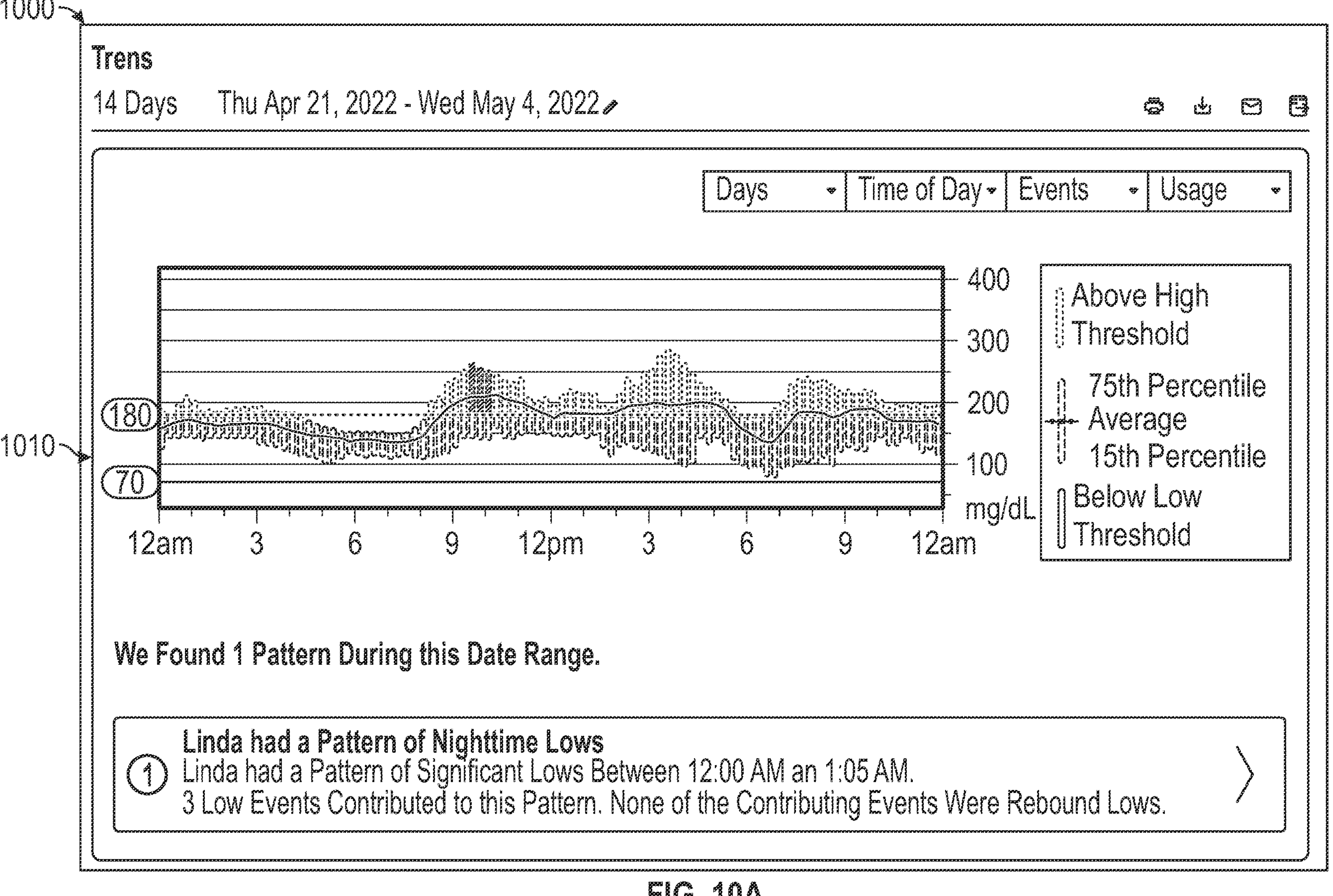
FIGS. 10A and 10B illustrate a trends feature displaying analyte concentration readings as a function of time for a normal target analyte concentration range and a pregnancy-specific target analyte concentration range, according to certain embodiments disclosed herein.
Figure 10B:
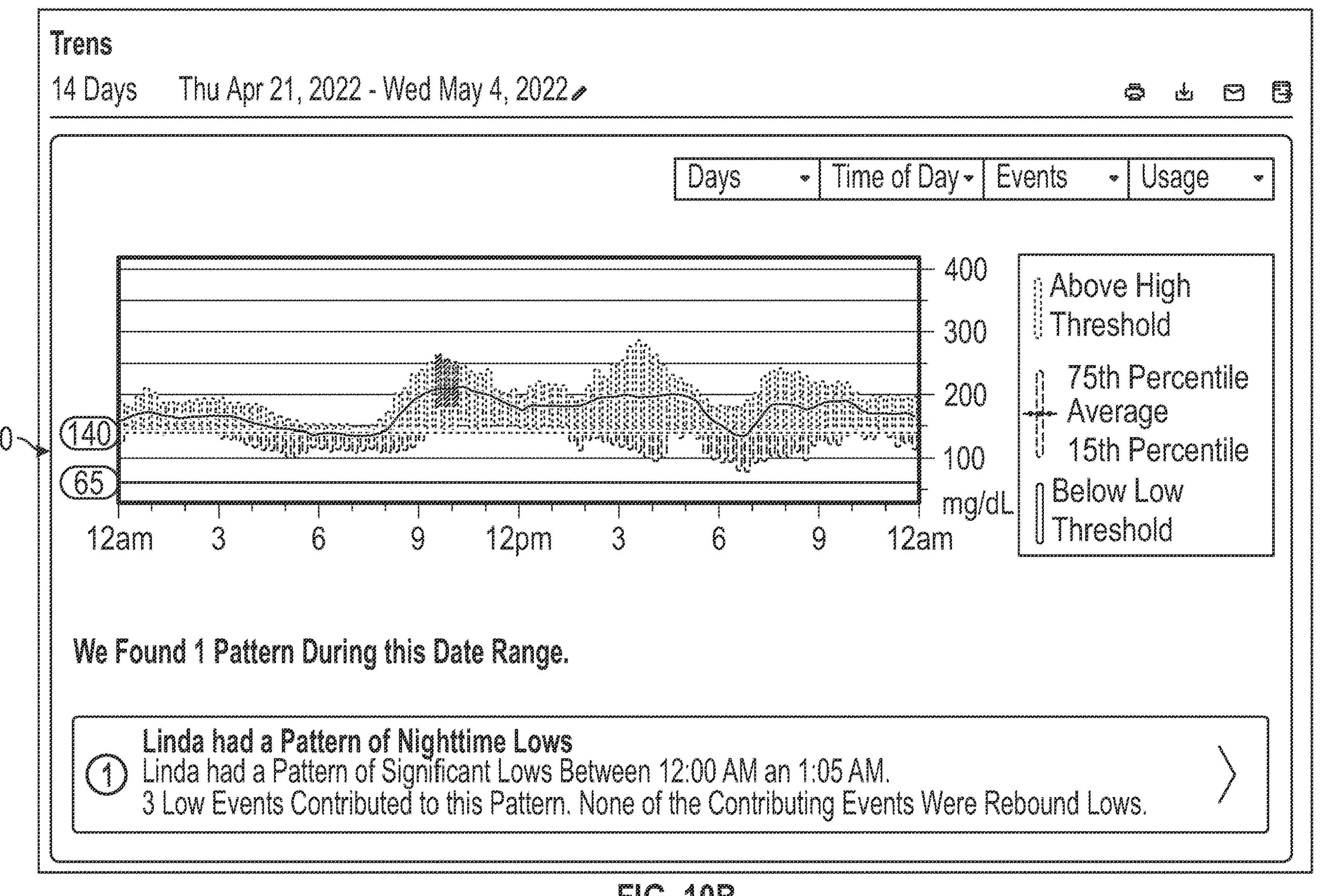
Figure 11:
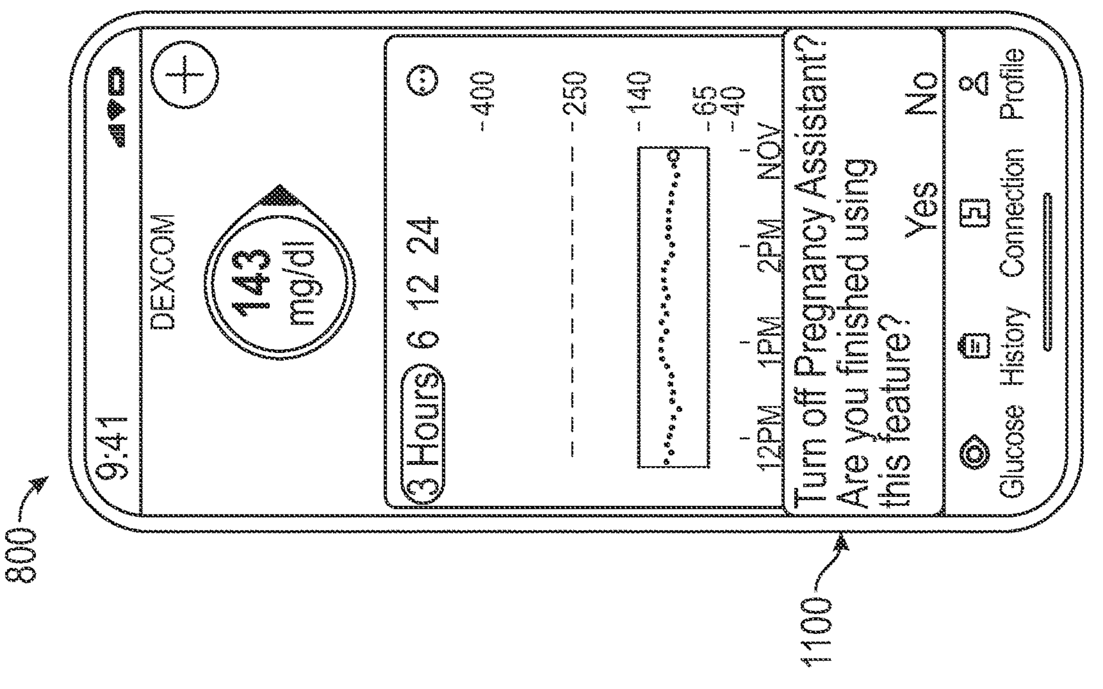
FIG. 11 illustrates a UI view including an option to disable a pregnancy assistant, according to certain embodiments disclosed herein.

The pregnancy assistant is then disabled after the due date, such as by automatically disabling the pregnancy assistant or providing the user with an option to disable the pregnancy assistant within a predetermined period of time after the due date has passed (e.g., FIGS. 7B and 11). Upon disabling the pregnancy assistant, one or more UI elements are automatically modified to revert back to the normal target analyte range and/or non-pregnancy-specific information (e.g., FIG. 5). These and other techniques are described below in further detail in conjunction with FIGS. 6A-12.

FIGS. 6A-6E illustrate an onboarding sequence that is presented to a user when enabling a pregnancy assistant, in accordance with some example aspects of the present disclosure. As shown, a user selects UI element 610 included in a connections dashboard 600 (FIG. 6A) and, in response, is presented with an onboarding sequence.

Figures 6A, 6B:
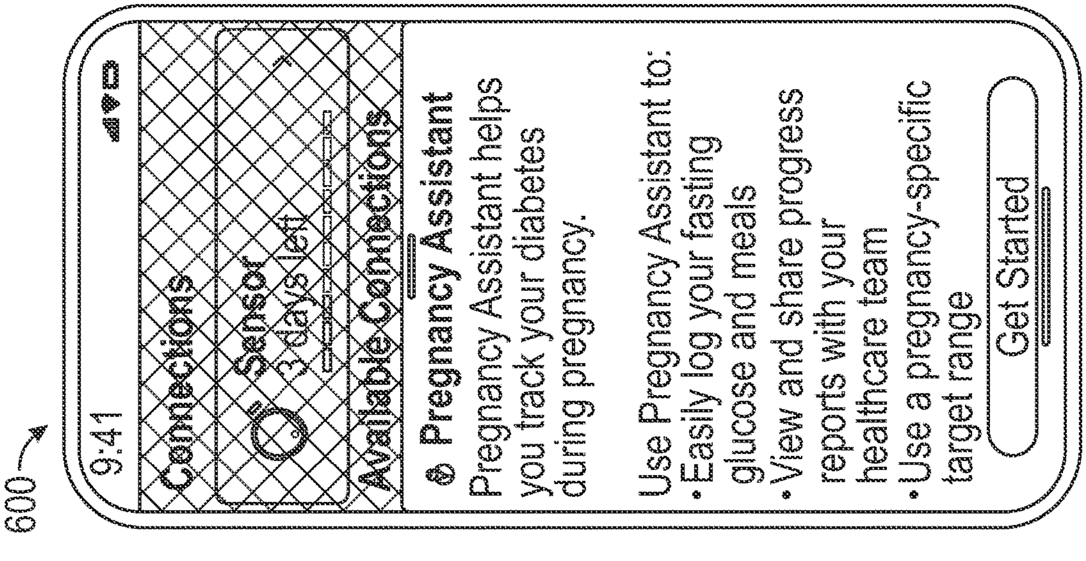
Figures 6C, 6D, 6E:
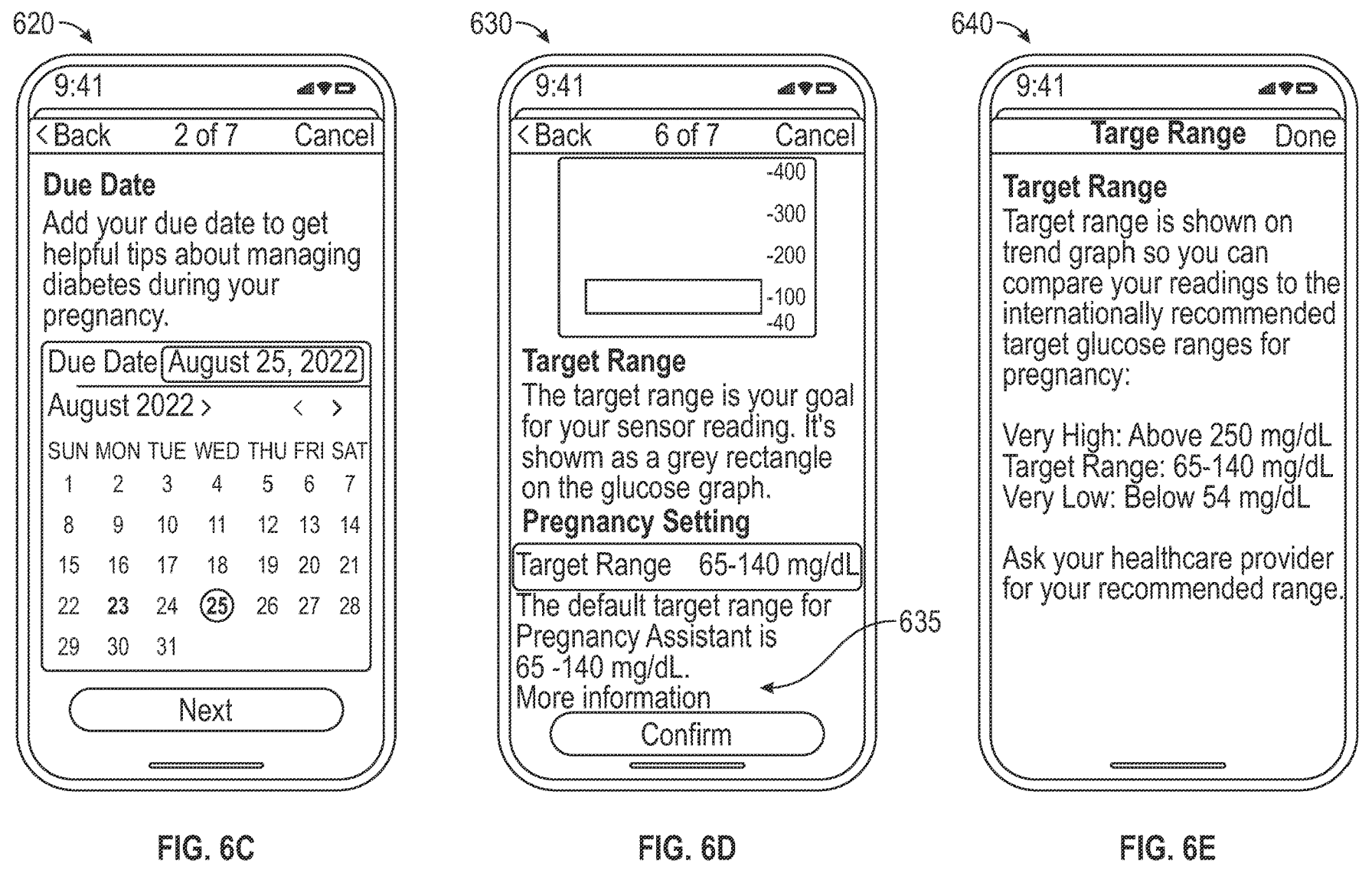

As part of the onboarding sequence, information related to features of the pregnancy assistant is displayed to the user (e.g., FIG. 6B). Additionally, a calendar UI element 620 is automatically displayed to enable a user to input a due date (e.g., FIG. 6C), and a target range UI element 630 is automatically displayed to enable a user to view and/or modify a pregnancy-specific target analyte range (e.g., a pregnancy-specific glucose concentration range) (e.g., FIG. 6D). Information 640 related to a pregnancy-specific target range analyte range may also be displayed to the user upon selection of a "more information" UI element 635 (e.g., FIG. 6E).

Upon enabling the pregnancy assistant, one or more UI elements are automatically modified to reflect a pregnancy-specific target analyte range and/or pregnancy-specific information. For example, as shown in FIG. 7A, connections dashboard 600 is automatically modified to include a pregnancy assistant UI element 710. In some embodiments, pregnancy assistant UI element 710 displays information indicating a gestational week (e.g., "Week 26"), a date range associated with a gestational week (e.g., Apr. 22, 2022-Apr. 29, 2022), and/or a due date for the pregnancy.

Figures 7D, 7E, 7F:
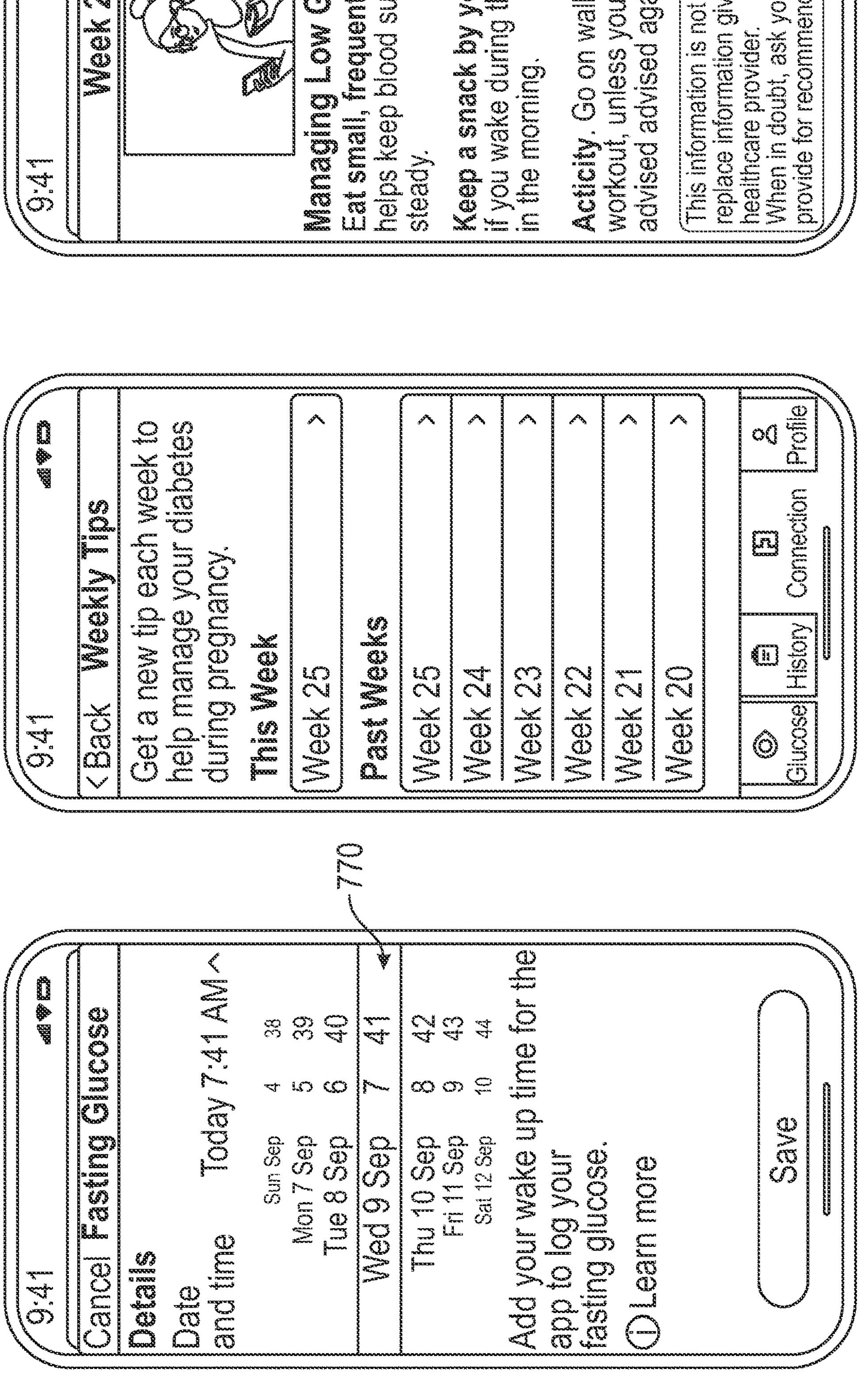

As shown in FIG. 7B, selecting the pregnancy assistant UI element 710 causes pregnancy assistant dashboard 720 to be displayed. As discussed above, key metrics related to managing diabetes during pregnancy include fasting glucose concentration values and post-meal glucose concentration values. Accordingly, upon selecting a post-meal glucose UI element 730, a user is presented with an option to select when post-meal analyte readings will be acquired. For example, as shown in FIG. 7C, a user may choose to log sensor readings associated with post-meal glucose concentration values at a particular post-meal duration of time, such as one, two, or three hours after each meal. Additionally, as shown in FIG. 7D, a user may be presented with a date/time UI element 770 to enable the user to select a wake-up time at which fasting analyte readings (e.g., fasting glucose concentration values) will be logged.

In various embodiments, during the onboarding sequence, a user selects a time at which they typically wake-up and one or more times at which they typically eat. In such embodiments, fasting glucose readings and post-meal glucose readings may then be automatically acquired (e.g., via SS 8) based on the wake-up and meal times inputted by the user. Additionally or alternatively, one or more reminders to log a wake-up time and/or meal times may be displayed to the user. In some embodiments, a user wake-up time may be automatically detected, such as based on accelerometer data (e.g., acquired by SS 8 or display device 150) and/or based on third-party data (e.g., data acquired via a user-worn activity tracker, etc.). Additionally or alternatively, one or more meal times may be automatically detected, such as based on glucose readings acquired by SS 8 and/or based on third-party data (e.g., data inputted into a meal-logging application, etc.). Further, in some embodiments, a wake-up time and/or one or more meal times may be automatically detected through one or more algorithms and/or analyte level patterns, such as a spike detection algorithm implemented by SS 8 and/or display device 150. A user may further be provided with an option to manually adjust wake-up and/or meal times that have been detected via any of the techniques described herein.

The pregnancy assistant dashboard 720 further enables a user to view educational resources related to gestational age. For example, upon selecting a weekly tips UI element 740, a user may be presented with educational information that corresponds to a current gestational week of the pregnancy, as shown in FIGS. 7E and 7F. The user may also be presented with an option to select and view educational information that corresponds to a past and/or future gestational week of the pregnancy. In some embodiments, gestational milestones are automatically displayed to the user based on gestational age (e.g., once a week, once every two weeks, once a month, etc.) to indicate whether the user is maintaining glucose levels within the pregnancy-specific target analyte concentration range, whether immediate attention is required, or whether adjustments to therapy are needed.

Figure 7H:
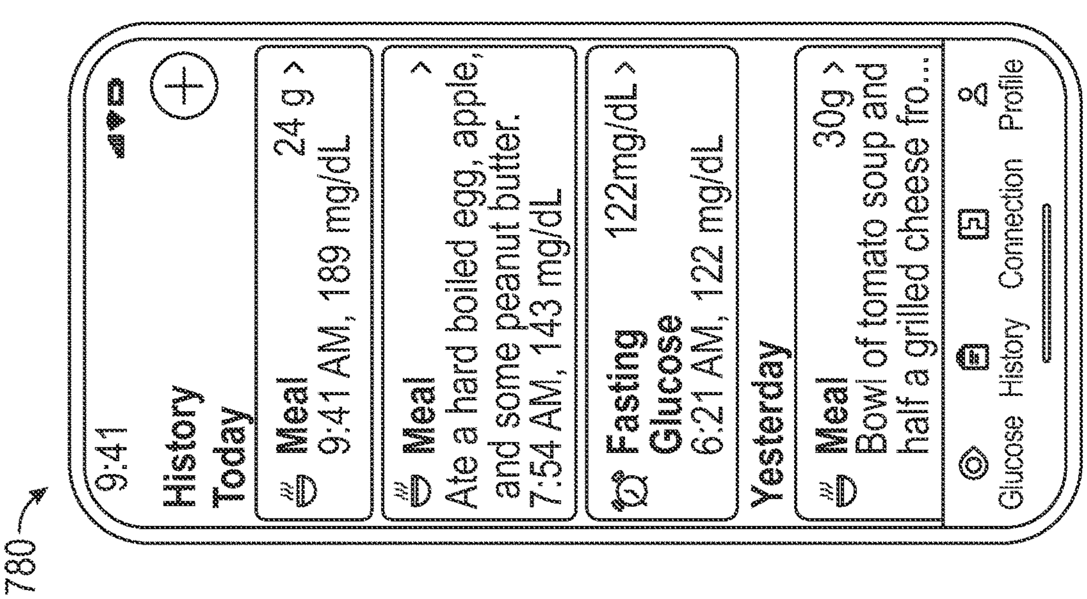
Figure 7G:
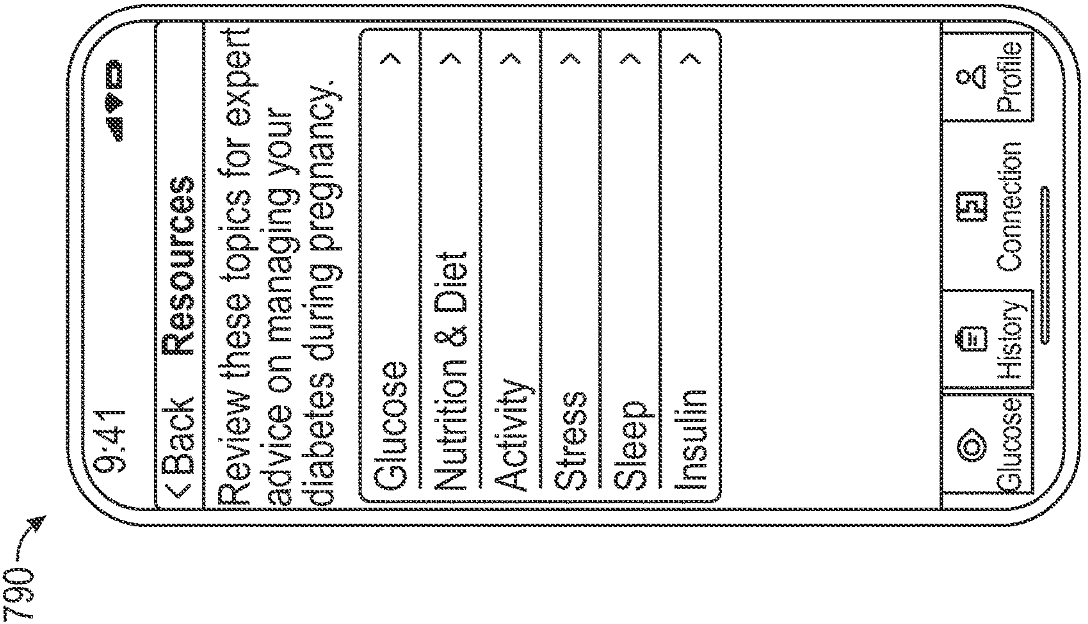

Upon selecting a resources UI element 750, a user may be presented with a variety of educational information 790 that includes advice on managing diabetes during pregnancy, as shown in FIG. 7G. Pregnancy assistant dashboard 720 may further include a UI element 760 that enables a user to disable the pregnancy assistant, as shown in FIG. 7B.

As shown in FIG. 7H, enabling the pregnancy assistant may cause a history dashboard 780 to be automatically generated and presented to a user. The history dashboard 780 enables a user to view pregnancy-specific information, including data related to meals (e.g., time of meal consumption, macronutrient amounts, textual descriptions of meals), analyte concentration readings corresponding to meals (e.g., post-meal glucose readings), fasting glucose readings, physical activity (e.g., exercise) performed by the user, medication intake, and/or illness/stress (e.g., a specific illness, a stressful event, etc.) experienced by the user. Enabling the pregnancy assistant may further cause the pregnancy-specific information (and/or reports that are prepared based on the pregnancy-specific information) to be automatically generated and transmitted to a HCP, in order to assist a pregnant patient in maintaining consistent logs of pregnancy-specific information, such as meals, post-meal glucose readings, and fasting glucose readings.

Figure 8B:
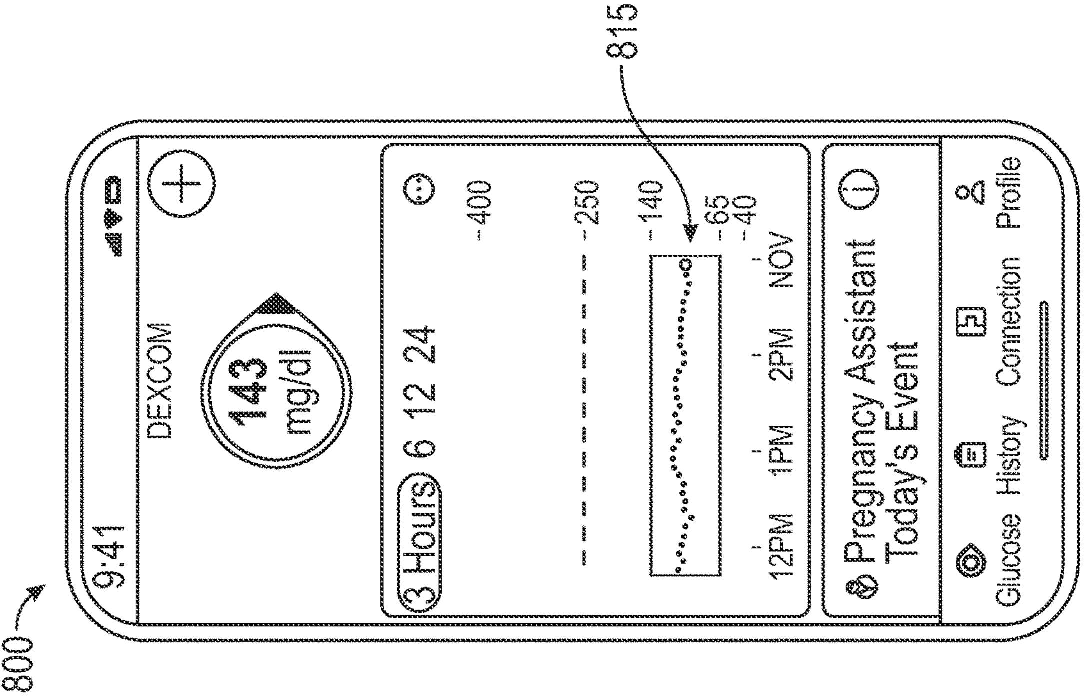
FIGS. 8A and 8B illustrate UI views displaying analyte concentration readings as a function of time for a normal target analyte concentration range and a pregnancy-specific target analyte concentration range, according to certain embodiments disclosed herein.
Figure 8A:
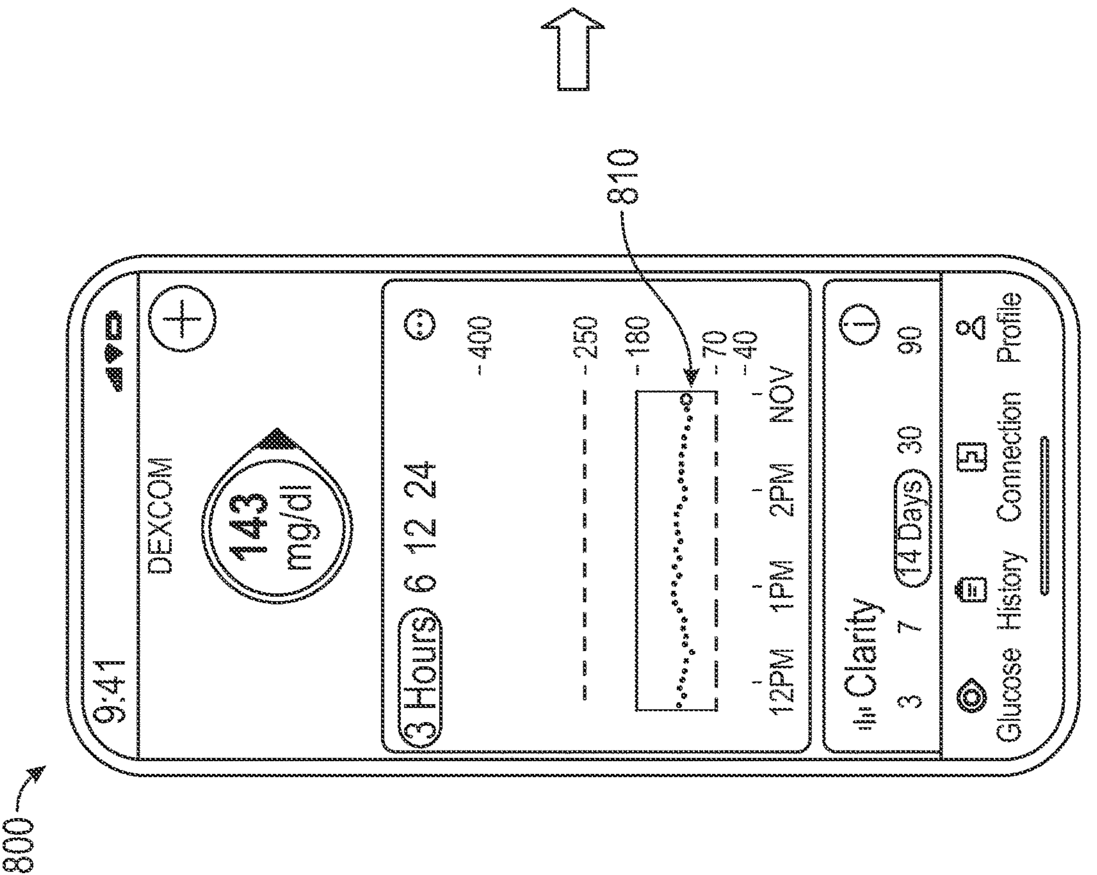

As discussed above, enabling the pregnancy assistant causes one or more target analyte ranges to be automatically modified to reflect pregnancy-specific target analyte ranges. In some embodiments, patterns and statistics identified by logic 420C and pattern detector 4201 may be presented in a performance report that implements pregnancy-specific target analyte ranges. For example, as shown in FIGS. 8A and 8B, upon enabling the pregnancy assistant, a UI view 800 displaying analyte concentration readings as a function of time (e.g., over a 3-hour period, 6-hour period, 12-hour, or 24-hour period) is automatically modified from displaying a normal target analyte concentration range 810 (e.g., 70-180 mg/dL, shown in FIG. 8A) to instead reflect a pregnancy-specific target analyte concentration range 815 (e.g., 65-140 mg/dL, shown in FIG. 8B).

Figure 9A:
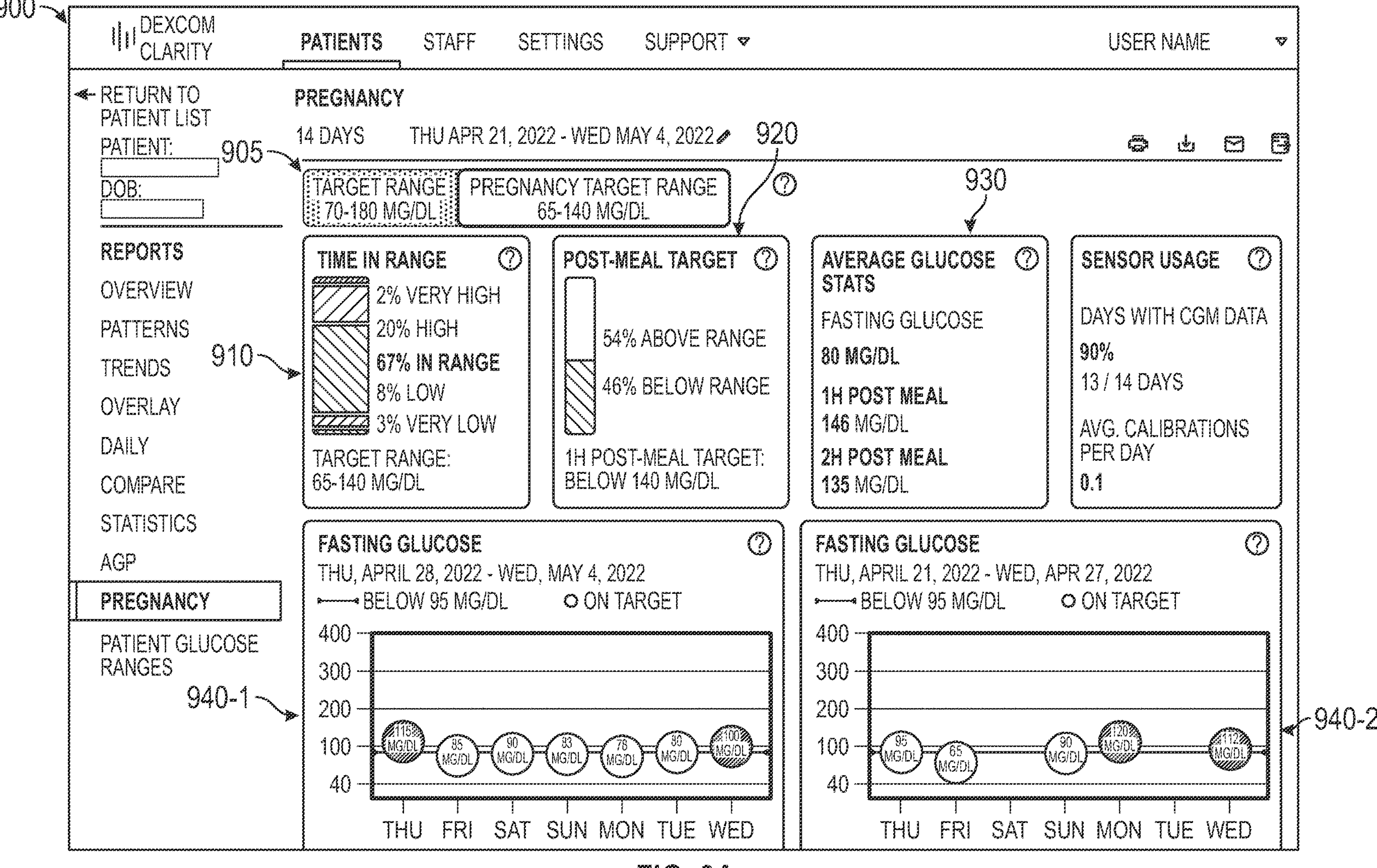
FIGS. 9A-9D illustrate widgets included in a performance report that have been updated to reflect a pregnancy-specific target analyte concentration range and pregnancy-specific information, according to certain embodiments disclosed herein.
Figure 9B:
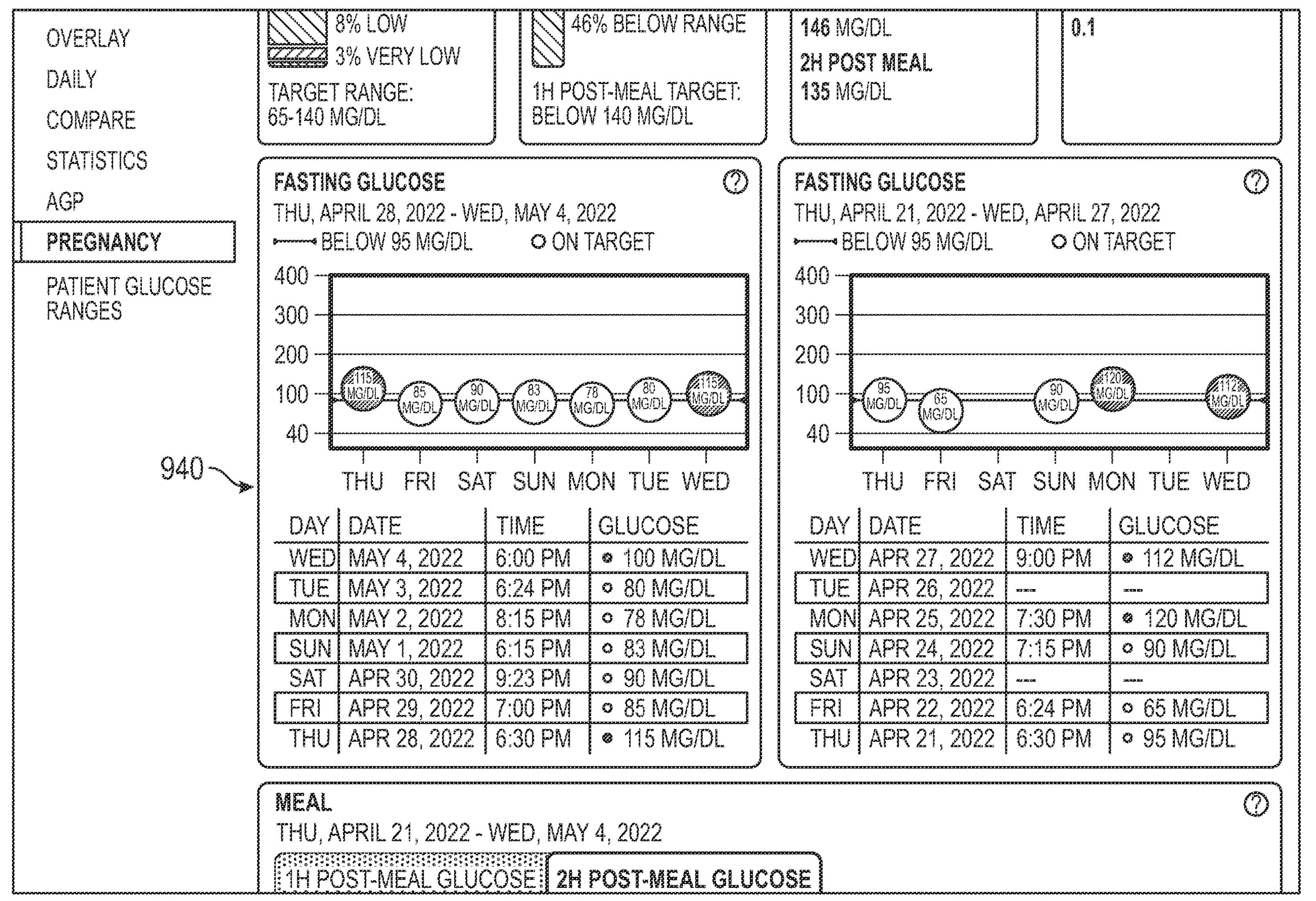
Figure 9C:
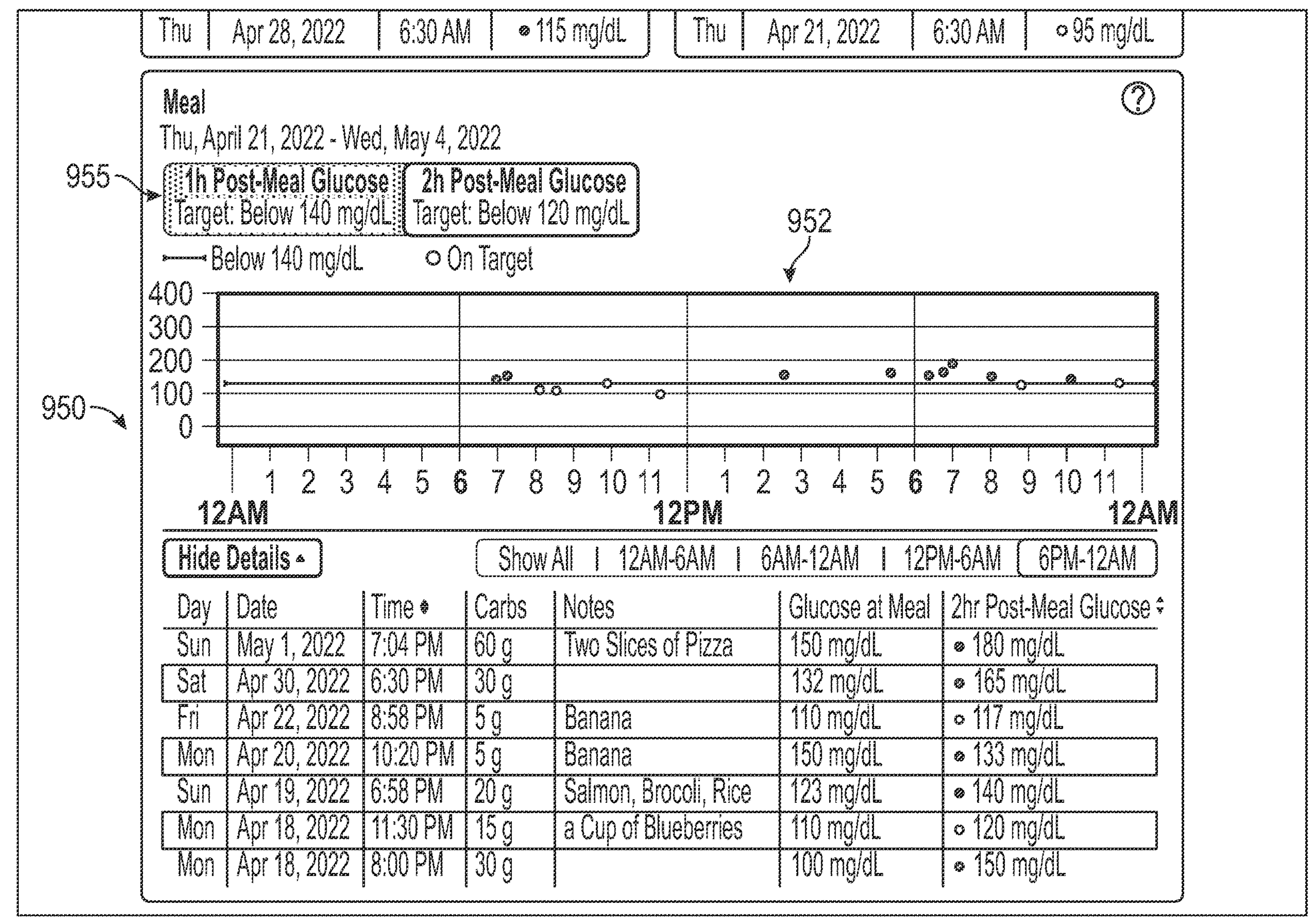
Figure 9D:
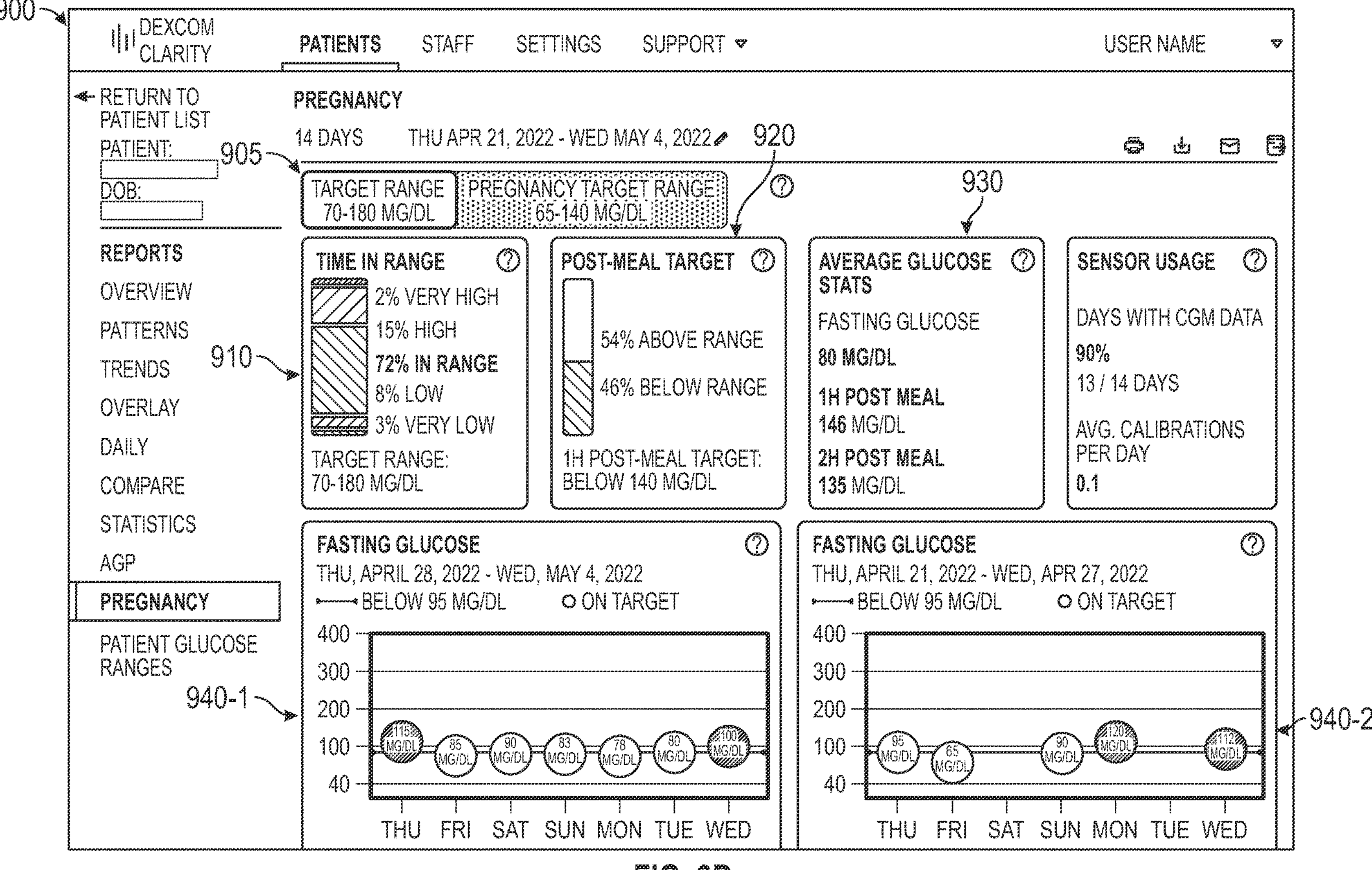

In another example, shown in FIGS. 9A-9C, upon enabling the pregnancy assistant, a UI view 900 displaying a time in range feature 910 and an analyte statistics feature 930 is automatically modified from displaying a normal target analyte concentration range (e.g., 70-180 mg/dL) to instead reflect a pregnancy-specific target analyte concentration range (e.g., 65-140 mg/dL). UI view 900 may further include a toggle UI element 905 that enables a user to switch between the normal target analyte concentration range and the pregnancy-specific target analyte concentration range. In some embodiments, the pregnancy-specific target analyte concentration range implemented in any of the reports, UI views, and widgets described herein may be automatically updated based on the due date of the user and/or gestational age of the pregnancy. For example, the pregnancy-specific target analyte concentration range may be automatically modified to reflect a tighter target analyte concentration range as the gestational age increases.

In response to a user interacting with toggle UI element 905, one or more widgets included in a performance report (e.g., UI view 900) are updated to reflect either the normal target analyte concentration range (FIG. 9D) or the pregnancy-specific target analyte concentration range (FIG. 9A). For example, upon interacting with toggle UI element 905 to select the pregnancy-specific target analyte concentration range, a stacked bar graph included in a time in range feature 910 is automatically modified to reflect a percentage of time that a user's analyte levels were in the pregnancy-specific target analyte concentration range.

In addition to modifying a target analyte concentration range, upon enabling the pregnancy assistant, one or more UI views may be automatically modified to present pregnancy-specific information and/or UI elements for tracking pregnancy-specific key metrics, such as by updating a UI view (e.g., UI view 900) to display a post-meal glucose UI element 920 and/or a fasting glucose UI element 940 (e.g., fasting glucose UI element 940-1 associated with a current week and fasting glucose UI element 940-2 associated with a prior week). In some embodiments, a post-meal glucose UI element 920 displays a stacked bar graph indicating how frequently a user's post-meal glucose concentration values were above or below an upper end of a pregnancy-specific analyte concentration threshold (e.g., 140 mg/dL). As shown in FIGS. 9A and 9B, a fasting glucose UI element 940 displays fasting glucose concentration values for a given period of time (e.g., for a prior 7-day period) and indicate (e.g., with color coding) whether each fasting glucose concentration value was above or below a target fasting glucose concentration value (e.g., 95 mg/dL).

Additionally, as shown in FIG. 9C, a post-meal glucose UI element 950 displays post-meal glucose concentration values for different meals consumed at different times on different days, enabling a user to view textual descriptions of the meals, the macronutrient (e.g., carbohydrate) content of each meal, glucose concentration values immediately after each meal, and whether post-meal glucose concentration values were above or below an upper end of a pregnancy-specific target analyte concentration range (e.g., 140 mg/dL for 1 hour post-meal or 120 mg/dL for 2 hours post-meal). In response to a user interacting with toggle UI element 955, a graph 952 plotting glucose concentration values as a function of time-of-day is updated to reflect either 1-hour post-meal glucose concentration values (e.g., 140 mg/dL) or 2-hour post-meal glucose concentration values (e.g., 120 mg/dL).

Further, one or more existing widgets may be automatically modified to include additional, pregnancy-specific information. For example, an existing analyte statistics feature 930 may be automatically modified from displaying an average glucose concentration value to displaying both fasting glucose concentration values (e.g., an average fasting glucose value) and post-meal glucose concentration values (e.g., 1 hour and 2 hours post-meal).

In a further example, shown in FIGS. 10A and 10B, upon enabling the pregnancy assistant, a UI view 1000 displaying a trends feature 1010 is automatically modified from displaying a normal target analyte concentration range (e.g., 70-180 mg/dL, as shown in FIG. 10A) to instead reflect a pregnancy-specific target analyte concentration range (e.g., 65-140 mg/dL, as shown in FIG. 10B). Other pregnancy-specific target analyte concentration ranges (e.g., 63-140 mg/dL, 63-137 mg/dL, 63-134 mg/dL, etc.) may be implemented in various embodiments. The trends feature 1010 of UI view 1000 includes a compilation of a user's time in range and may be presented as a scatter plot with a line of best fit identifying a user's time in range trend over a period of time (e.g., a 24-hour period in the example shown) for a specified period (e.g., any continuous 14-day period in the example shown).

In various embodiments, the pregnancy assistant is disabled automatically on the due date, within a predetermined period of time after the due date has passed, or upon detecting that the user has given birth (e.g., based on detecting changes to one or more analyte values of the user). In some embodiments, a user is presented with an option 1100 to disable the pregnancy assistant on or within a predetermined period of time after the due date, as shown in FIG. 11. Further, in some embodiments, the pregnancy assistant is disabled (e.g., automatically or based on presenting an option to disable to the user) when a determination is made that the user does not have gestational diabetes. For example, the pregnancy assistant may be automatically disabled (or an option to disable the pregnancy assistant may be presented to the user) when the user's glucose levels remain within a normal target analyte concentration range for a predetermined period of time. Further, in some embodiments, in response to detecting abnormally high glucose concentration values post-partum (e.g., within a 6-week post-partum period), a message may be automatically displayed to the user (and/or transmitted and displayed to an HCP of the user) indicating that a remedial action should be taken.

Upon disabling the pregnancy assistant, one or more UI elements (e.g., time in range feature 910, trends feature 1010, etc.) are automatically modified from the pregnancy-specific target analyte range and/or pregnancy-specific information to reflect a normal target analyte range and/or non-pregnancy-specific information. Additionally or alternatively, one or more widgets (e.g., post-meal glucose UI element 920, fasting glucose UI element 940, etc.) that include pregnancy-specific information and/or key metrics are removed from one or more UI views.

In some embodiments, pregnancy-specific information may be removed from one or more widgets. For example, information reflecting a fasting glucose concentration value and one or more post-meal glucose concentration values may be removed from analyte statistics feature 930, and analyte statistics feature 930 may instead revert to displaying an average glucose concentration value (e.g., as shown in analyte statistics feature 520 of FIG. 5).

Figure 12:
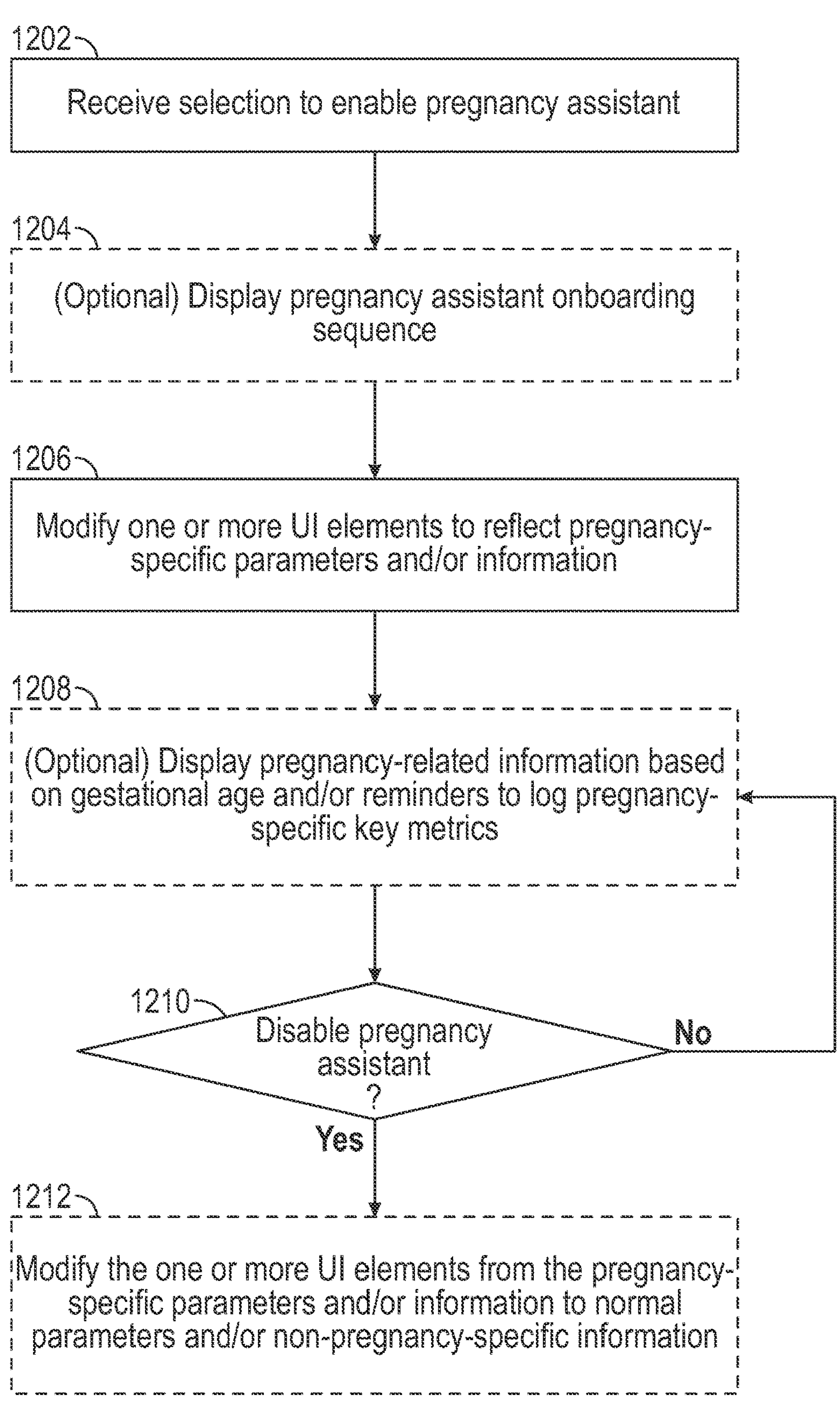
FIGS. 12 and 13 are flow diagrams illustrating example operations for generating user interface views associated with sensor data representative of glucose concentration level(s) in one or more users, according to certain embodiments disclosed herein.

Example Operations for Tracking, Reporting, and Visualizing Pregnancy-Related Analyte Data FIG. 12 is a flow diagram illustrating example operations 1200 for generating a user interface view associated with sensor data representative of glucose concentration level(s) in a user, in accordance with some example aspects of the present disclosure. Operations 1200 may be performed by a processing system, such as the analyte processor 135. In some examples, the operations 1200 may be used for generating one or more of the reports illustrated in FIGS. 5-11 as described in further detail below.

Operations 1200 may begin, at 1202, by receiving a selection to enable a pregnancy assistant. For example, a user may select UI element 610 included in the connections dashboard 600 shown in FIG. 6A.

At 1204, an onboarding sequence is optionally displayed to the user. For example, during presentation of the onboarding sequence, information related to features of the pregnancy assistant may be displayed to the user, and/or one or more UI elements may be automatically displayed to enable the user to input a due date and to view and/or modify a pregnancy-specific target analyte range.

At 1206, one or more UI elements are automatically modified to reflect pregnancy-specific parameters and/or pregnancy-specific information. For example, one or more UI views including one or more widgets (e.g., a time in range feature 510, a trends feature 540, etc.) may be automatically modified from displaying a normal target analyte concentration range to instead reflect a pregnancy-specific target analyte concentration range, and/or one or more UI views may be automatically modified to add pregnancy-specific widgets (e.g., a post-meal glucose UI element 920 and/or a fasting glucose UI element 940). U.S. App. No. 2022/0265224, which is incorporated herein in its entirety by reference, further describes techniques for generating various types of reports, UI views, and widgets that, in certain embodiments, may be implemented in connection with operations 1200.

At 1208, pregnancy-related information is optionally displayed to the user automatically, for example, based on gestational age (e.g., FIGS. 7E-7G). Additionally or alternatively, reminders to log pregnancy-specific key metrics (e.g., fasting glucose levels and/or post-meal glucose levels) are displayed to the user.

At 1210, the pregnancy assistant may be disabled, for example, based on the due date. For example, the pregnancy assistant may be disabled automatically on the due date, within a predetermined period of time after the due date has passed, or upon detecting that the user has given birth.

If, at 1210, the pregnancy assistant is disabled, then, at 1212, one or more UI elements are automatically modified from the pregnancy-specific target analyte range and/or pregnancy-specific information to reflect a normal target analyte range and/or non-pregnancy-specific information. For example, one or more widgets that include pregnancy-specific information may be removed from one or more UI views, and/or one or more widgets may be modified to remove pregnancy-specific information.

Figure 13:
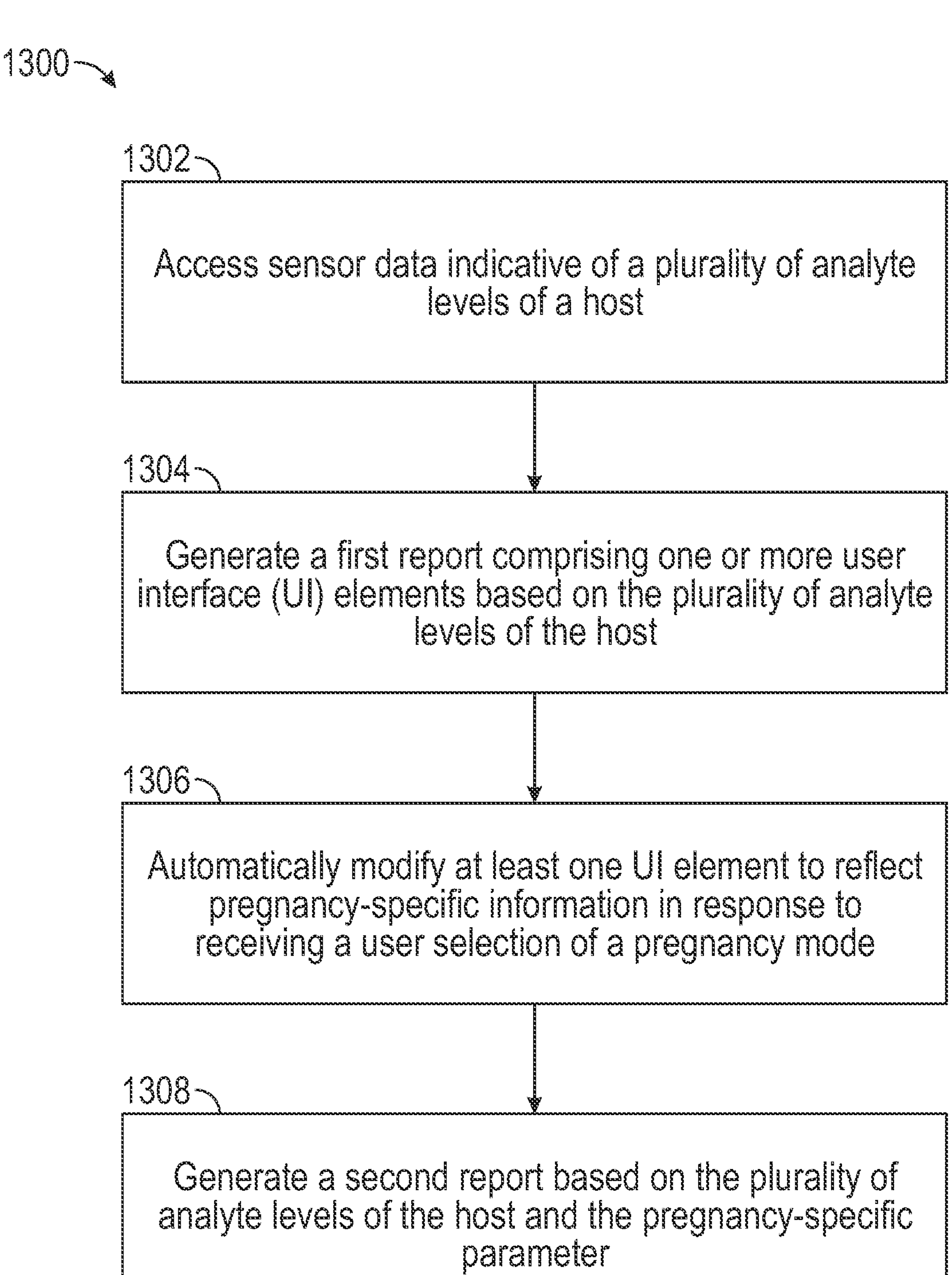

FIG. 13 is a flow diagram illustrating example operations 1300 for generating a user interface view associated with sensor data representative of glucose concentration level(s) in a user, in accordance with some example aspects of the present disclosure. Operations 1300 may be performed by a processing system, such as the analyte processor 135. In some examples, the operations 1300 may be used for generating one or more of the reports illustrated in FIGS. 5-11, as described in further detail below.

Operations 1300 may begin, at 1302, by accessing sensor data including a plurality of analyte readings of the host during a plurality of time periods. Each analyte reading is indicative of an analyte level of the host at a respective time. At 1304, a first user interface (UI) view (e.g., a first report) comprising one or more UI elements is generated based on the plurality of analyte levels of the host.

Next, at 1306, in response to receiving a user selection of a pregnancy mode, at least one UI element included in the one or more UI elements is automatically modified to reflect pregnancy-specific information, such as a pregnancy-specific parameter (e.g., a pregnancy-specific analyte concentration range). At 1308, a second UI view (e.g., a second report) is generated based on the plurality of analyte levels of the host and the pregnancy-specific parameter.

Example Clauses

Implementation examples are described in the following numbered clauses:

Clause 1: A method for generating a user interface view including sensor data representative of analyte levels of a host, comprising: accessing sensor data including a plurality of analyte readings of the host during a plurality of time periods, wherein each analyte reading is indicative of an analyte level of the host at a respective time; generating a first user interface (UI) view comprising one or more UI elements based on the plurality of analyte levels of the host; in response to receiving a user selection of a pregnancy mode, automatically modifying a parameter of at least one UI element included in the one or more UI elements to reflect a pregnancy-specific parameter; and generating a second UI view based on the plurality of analyte levels of the host and the pregnancy-specific parameter.

Clause 2: The method of Clause 1, wherein the pregnancy-specific parameter comprises a pregnancy-specific analyte range.

Clause 3: The method of any of Clauses 1 or 2, wherein the pregnancy-specific analyte range comprises a pregnancy-specific glucose concentration range.

Clause 4: The method of any of Clauses 1-3, further comprising, in response to disabling the pregnancy mode, automatically reverting the parameter of the at least one UI element from the pregnancy-specific parameter to a non-pregnancy-specific parameter.

Clause 5: The method of any of Clauses 1-4, further comprising, after disabling the pregnancy mode, generating a third UI view based on the plurality of analyte levels of the host and the non-pregnancy-specific parameter.

Clause 6: The method of any of Clauses 1-5, further comprising receiving input corresponding to a host due date, wherein disabling the pregnancy mode is performed automatically based on determining that the host due date has passed.

Clause 7: The method of any of Clauses 1-6, further comprising: receiving input corresponding to a host due date; and causing an option to disable the pregnancy mode to be displayed within a predetermined period of time of the host due date.

Clause 8: The method of any of Clauses 1-7, further comprising: receiving input corresponding to a host due date; determining a gestational age based on the host due date; and causing a UI element corresponding to the gestational age to be displayed.

Clause 9: The method of any of Clauses 1-8, wherein the user selection of the pregnancy mode comprises switching a toggle UI element from a normal analyte range to the pregnancy-specific analyte range.

Clause 10: The method of any of Clauses 1-9, wherein automatically modifying the parameter of the at least one UI element comprises updating a time in range widget to reflect the pregnancy-specific analyte range.

Clause 11: The method of any of Clauses 1-10, further comprising, in response to receiving the user selection of the pregnancy mode, causing at least one of (i) a reminder to log a fasting glucose reading to be displayed, or (ii) a reminder to log a post-meal glucose reading to be displayed.

Clause 12: A method for generating a user interface view including sensor data representative of analyte levels of a host, comprising: accessing sensor data including a plurality of analyte readings of the host during a plurality of time periods, wherein each analyte reading is indicative of an analyte level of the host at a respective time; generating a first user interface (UI) view comprising one or more UI elements based on the plurality of analyte levels of the host; in response to receiving a user selection of a pregnancy mode, automatically modifying at least one UI element included in the one or more UI elements to reflect pregnancy-specific information; and generating a second UI view based on the plurality of analyte levels of the host and the pregnancy-specific information.

Clause 13: The method of Clause 12, wherein automatically modifying the at least one UI element to reflect the pregnancy-specific information comprises causing a UI element corresponding to at least one of a fasting glucose value or a post-meal glucose value to be displayed.

Clause 14: The method of any of Clauses 12 or 13, further comprising: receiving input corresponding to a host due date; and determining a gestational age based on the host due date, wherein automatically modifying the at least one UI element to reflect the pregnancy-specific information comprises causing a UI element related to the gestational age to be displayed.

Clause 15: The method of any of Clauses 12-14, wherein the UI element related to the gestational age comprises educational information corresponding to the gestational age.

Clause 16: The method of any of Clauses 12-15, wherein automatically modifying the at least one UI element to reflect the pregnancy-specific information comprises causing at least one of (i) a reminder to log a fasting glucose reading to be displayed, or (ii) a reminder to log a post-meal glucose reading to be displayed.

Clause 17: The method of any of Clauses 12-16, wherein automatically modifying the at least one UI element to reflect the pregnancy-specific information comprises causing an onboarding sequence including a prompt to enter a due date to be displayed.

Clause 18: The method of any of Clauses 12-17, further comprising, in response to disabling the pregnancy mode, automatically removing the pregnancy-specific information associated with the at least one UI element.

Clause 19: The method of any of Clauses 12-18, further comprising receiving input corresponding to a host due date, wherein disabling the pregnancy mode is performed automatically based on determining that the host due date has passed.

Clause 20: The method of any of Clauses 12-19, further comprising: receiving input corresponding to a host due date; and causing an option to disable the pregnancy mode to be displayed within a predetermined period of time of the host due date.

ADDITIONAL CONSIDERATIONS

Each of these non-limiting examples can stand on its own or can be combined in various permutations or combinations with one or more of the other examples. The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "of" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A method for generating a user interface view including sensor data representative of analyte levels of a host, comprising:

accessing sensor data including a plurality of analyte readings of the host during a plurality of time periods, wherein each analyte reading is indicative of an analyte level of the host at a respective time;

generating a first user interface (UI) view comprising one or more UI elements based on the plurality of analyte levels of the host;

in response to receiving a user selection of a pregnancy mode, automatically modifying a parameter of at least one UI element included in the one or more UI elements to reflect a pregnancy-specific parameter;

generating a second UI view based on the plurality of analyte levels of the host and the pregnancy-specific parameter; and in response to disabling the pregnancy mode, automatically reverting the parameter of the at least one UI element from the pregnancy-specific parameter to a non-pregnancy-specific parameter.

2. The method of claim 1, wherein the pregnancy-specific parameter comprises a pregnancy-specific analyte range.

3. The method of claim 2, wherein the pregnancy-specific analyte range comprises a pregnancy-specific glucose concentration range.

4. The method of claim 1, further comprising, after disabling the pregnancy mode, generating a third UI view based on the plurality of analyte levels of the host and the non-pregnancy-specific parameter.

5. The method of claim 1, further comprising receiving input corresponding to a host due date, wherein disabling the pregnancy mode is performed automatically based on determining that the host due date has passed.

6. The method of claim 1, further comprising:

receiving input corresponding to a host due date; and causing an option to disable the pregnancy mode to be displayed within a predetermined period of time of the host due date.

7. The method of claim 1, further comprising:

receiving input corresponding to a host due date;

determining a gestational age based on the host due date; and causing a UI element corresponding to the gestational age to be displayed.

8. The method of claim 2, wherein the user selection of the pregnancy mode comprises switching a toggle UI element from a normal analyte range to the pregnancy-specific analyte range.

9. The method of claim 8, wherein automatically modifying the parameter of the at least one UI element comprises updating a time in range widget to reflect the pregnancy-specific analyte range.

10. The method of claim 1, further comprising, in response to receiving the user selection of the pregnancy mode, causing at least one of (i) a reminder to log a fasting glucose reading to be displayed, or (ii) a reminder to log a post-meal glucose reading to be displayed.

11. A method for generating a user interface view including sensor data representative of analyte levels of a host, comprising:

accessing sensor data including a plurality of analyte readings of the host during a plurality of time periods, wherein each analyte reading is indicative of an analyte level of the host at a respective time;

generating a first user interface (UI) view comprising one or more UI elements based on the plurality of analyte levels of the host;

in response to receiving a user selection of a pregnancy mode, automatically modifying at least one UI element included in the one or more UI elements to reflect pregnancy-specific information;

generating a second UI view based on the plurality of analyte levels of the host and the pregnancy-specific information; and in response to disabling the pregnancy mode, automatically removing the pregnancy-specific information associated with the at least one UI element.

12. The method of claim 11, wherein automatically modifying the at least one UI element to reflect the pregnancy-specific information comprises causing a UI element corresponding to at least one of a fasting glucose value or a post-meal glucose value to be displayed.

13. The method of claim 11, further comprising:

receiving input corresponding to a host due date; and determining a gestational age based on the host due date, wherein automatically modifying the at least one UI element to reflect the pregnancy-specific information comprises causing a UI element related to the gestational age to be displayed.

14. The method of claim 13, wherein the UI element related to the gestational age comprises educational information corresponding to the gestational age.

15. The method of claim 11, wherein automatically modifying the at least one UI element to reflect the pregnancy-specific information comprises causing at least one of (i) a reminder to log a fasting glucose reading to be displayed, or (ii) a reminder to log a post-meal glucose reading to be displayed.

16. The method of claim 11, wherein automatically modifying the at least one UI element to reflect the pregnancy-specific information comprises causing an onboarding sequence including a prompt to enter a due date to be displayed.

17. The method of claim 11, further comprising receiving input corresponding to a host due date, wherein disabling the pregnancy mode is performed automatically based on determining that the host due date has passed.

18. The method of claim 11, further comprising:

receiving input corresponding to a host due date; and causing an option to disable the pregnancy mode to be displayed within a predetermined period of time of the host due date.

* * * * *